US012290268B2

(12) United States Patent
Sariibrahimoglu et al.

(10) Patent No.: US 12,290,268 B2
(45) Date of Patent: May 6, 2025

(54) SHOCKWAVE CATHETERS FOR TREATING RHINOSINUSITIS

(71) Applicant: Shockwave Medical, Inc., Santa Clara, CA (US)

(72) Inventors: Kemal Sariibrahimoglu, Santa Clara, CA (US); Thomas Charles Hasenberg, Campbell, CA (US); Show-Mean Steve Wu, Santa Clara, CA (US)

(73) Assignee: SHOCKWAVE MEDICAL, INC., Santa Clara, CA (US)

( * ) Notice: Subject to any disclaimer, the term of this patent is extended or adjusted under 35 U.S.C. 154(b) by 0 days.

(21) Appl. No.: 18/620,583

(22) Filed: Mar. 28, 2024

(65) Prior Publication Data
US 2024/0325032 A1 Oct. 3, 2024

Related U.S. Application Data

(60) Provisional application No. 63/456,272, filed on Mar. 31, 2023.

(51) Int. Cl.
A61B 17/00 (2006.01)
A61B 17/16 (2006.01)
A61B 90/00 (2016.01)

(52) U.S. Cl.
CPC .... A61B 17/1657 (2013.01); A61B 17/00234 (2013.01); A61B 17/1679 (2013.01);
(Continued)

(58) Field of Classification Search
CPC .......... A61B 17/1657; A61B 17/00234; A61B 17/1679; A61B 17/1688;
(Continued)

(56) References Cited

U.S. PATENT DOCUMENTS 2,916,647 A  12/1959 George
3,412,288 A  11/1968 Ostrander
(Continued)

FOREIGN PATENT DOCUMENTS

AU  2104414 A1  2/1995
AU  2009313507 B2  11/2014
(Continued)

OTHER PUBLICATIONS

Kaplan, Dr. M. (2020, Jan. 29). How long does The balloon sinuplasty procedure take ?. Kaplan Sinus Relief. https://www.kaplansinusrelief.com/blog/how-long-does-balloon-sinuplasty-procedure-take/ (Year: 2021).*
(Continued)

Primary Examiner — Lynsey C Eiseman
Assistant Examiner — Skylar Lindsey Christianson
(74) Attorney, Agent, or Firm — Morrison & Foerster LLP

(57) ABSTRACT

Described herein is a method for treating a narrowed region of a lumen in the ear or nose of a patient. The method includes advancing a catheter within the lumen such that a distal end of the catheter is positioned proximate to the narrowed region, filling a fillable member to expand the fillable member within the lumen, and generating at least one shock wave from at least one shock wave emitter. The at least one shock wave creates one or more fractures in a bony structure of the narrowed region of the lumen that dilate the narrowed region.

21 Claims, 7 Drawing Sheets

(52) U.S. Cl.
CPC .......... *A61B 17/1688* (2013.01); *A61B 90/08* (2016.02); *A61B 90/361* (2016.02); *A61B 2017/00238* (2013.01); *A61B 2017/00292* (2013.01); *A61B 2017/00411* (2013.01); *A61B 2090/0807* (2016.02); *A61B 2217/007* (2013.01)

(58) Field of Classification Search
CPC .......... A61B 2017/00238; A61B 2017/00292; A61B 2017/00411; A62B 90/08; A62B 90/361
See application file for complete search history.

(56) References Cited

U.S. PATENT DOCUMENTS

| | | | |
|---|---|---|---|
| 3,413,976 A | 12/1968 | Roze |
| 3,524,101 A | 8/1970 | Barbini |
| 3,583,766 A | 6/1971 | Padberg |
| 3,785,382 A | 1/1974 | Schmidt-Kloiber et al. |
| 3,902,499 A | 9/1975 | Shene |
| 3,942,531 A | 3/1976 | Hoff et al. |
| 4,027,674 A | 6/1977 | Tessler et al. |
| 4,030,505 A | 6/1977 | Tessler |
| 4,445,509 A | 5/1984 | Auth |
| 4,662,126 A | 5/1987 | Malcolm |
| 4,662,375 A | 5/1987 | Hepp et al. |
| 4,671,254 A | 6/1987 | Fair |
| 4,685,458 A | 8/1987 | Leckrone |
| 4,741,405 A | 5/1988 | Moeny et al. |
| 4,809,682 A | 3/1989 | Forssmann et al. |
| 4,813,934 A | 3/1989 | Engelson et al. |
| 4,878,495 A | 11/1989 | Grayzei |
| 4,890,603 A | 1/1990 | Filler |
| 4,900,303 A | 2/1990 | Lemelson |
| 4,990,134 A | 2/1991 | Auth |
| 4,994,032 A | 2/1991 | Sugiyama et al. |
| 5,009,232 A | 4/1991 | Hassler et al. |
| 5,046,503 A | 9/1991 | Schneiderman |
| 5,057,103 A | 10/1991 | Davis |
| 5,057,106 A | 10/1991 | Kasevich et al. |
| 5,061,240 A | 10/1991 | Cherian |
| 5,078,717 A | 1/1992 | Parins et al. |
| 5,102,402 A | 4/1992 | Dror et al. |
| 5,103,804 A | 4/1992 | Abele et al. |
| 5,116,227 A | 5/1992 | Levy |
| 5,152,767 A | 10/1992 | Sypal et al. |
| 5,152,768 A | 10/1992 | Bhatta |
| 5,154,722 A | 10/1992 | Filip et al. |
| 5,176,675 A | 1/1993 | Watson et al. |
| 5,195,508 A | 3/1993 | Muller et al. |
| 5,245,988 A | 9/1993 | Einars et al. |
| 5,246,447 A | 9/1993 | Rosen et al. |
| 5,254,121 A | 10/1993 | Manevitz et al. |
| 5,281,231 A | 1/1994 | Rosen et al. |
| 5,295,958 A | 3/1994 | Shturman |
| 5,304,134 A | 4/1994 | Kraus et al. |
| 5,321,715 A | 6/1994 | Trost |
| 5,324,255 A | 6/1994 | Passafaro et al. |
| 5,336,234 A | 8/1994 | Vigil et al. |
| 5,362,309 A | 11/1994 | Carter |
| 5,364,393 A | 11/1994 | Auth et al. |
| 5,368,591 A | 11/1994 | Lennox et al. |
| 5,395,335 A | 3/1995 | Jang |
| 5,417,208 A | 5/1995 | Winkler |
| 5,425,735 A | 6/1995 | Rosen et al. |
| 5,454,809 A | 10/1995 | Janssen |
| 5,472,406 A | 12/1995 | de la Torre et al. |
| 5,582,578 A | 12/1996 | Zhong et al. |
| 5,584,843 A | 12/1996 | Wulfman et al. |
| 5,603,731 A | 2/1997 | Whitney |
| 5,609,606 A | 3/1997 | O'Boyle |
| 5,662,590 A | 9/1997 | de la Torre et al. |
| 5,709,676 A | 1/1998 | Alt |
| 5,846,218 A | 12/1998 | Brisken et al. |
| 5,891,089 A | 4/1999 | Katz et al. |
| 5,893,840 A | 4/1999 | Hull et al. |
| 5,931,805 A | 8/1999 | Brisken |
| 6,007,530 A | 12/1999 | Dornhofer et al. |
| 6,033,371 A | 3/2000 | Torre et al. |
| 6,056,722 A | 5/2000 | Jayaraman |
| 6,080,119 A | 6/2000 | Schwarze et al. |
| 6,083,232 A | 7/2000 | Cox |
| 6,090,104 A | 7/2000 | Webster et al. |
| 6,113,560 A | 9/2000 | Simnacher |
| 6,132,444 A | 10/2000 | Shturman et al. |
| 6,146,358 A | 11/2000 | Rowe |
| 6,186,963 B1 | 2/2001 | Schwarze et al. |
| 6,210,408 B1 | 4/2001 | Chandrasekaran et al. |
| 6,215,734 B1 | 4/2001 | Moeny et al. |
| 6,217,531 B1 | 4/2001 | Reitmajer |
| 6,267,747 B1 | 7/2001 | Samson et al. |
| 6,277,138 B1 | 8/2001 | Levinson et al. |
| 6,287,272 B1 | 9/2001 | Brisken et al. |
| 6,352,535 B1 | 3/2002 | Lewis et al. |
| 6,364,894 B1 | 4/2002 | Healy et al. |
| 6,367,203 B1 | 4/2002 | Graham et al. |
| 6,371,971 B1 | 4/2002 | Tsugita et al. |
| 6,398,792 B1 | 6/2002 | O'Connor |
| 6,406,486 B1 | 6/2002 | de la Torre et al. |
| 6,440,124 B1 | 8/2002 | Esch et al. |
| 6,494,890 B1 | 12/2002 | Shturman et al. |
| 6,514,203 B2 | 2/2003 | Bukshpan |
| 6,524,251 B2 | 2/2003 | Rabiner et al. |
| 6,589,253 B1 | 7/2003 | Cornish et al. |
| 6,607,003 B1 | 8/2003 | Wilson |
| 6,638,246 B1 | 10/2003 | Naimark et al. |
| 6,652,547 B2 | 11/2003 | Rabiner et al. |
| 6,666,834 B2 | 12/2003 | Restle et al. |
| 6,689,089 B1 | 2/2004 | Tiedtke et al. |
| 6,736,784 B1 | 5/2004 | Menne et al. |
| 6,740,081 B2 | 5/2004 | Hilal |
| 6,755,821 B1 | 6/2004 | Fry |
| 6,939,320 B2 | 9/2005 | Lennox |
| 6,989,009 B2 | 1/2006 | Lafontaine |
| 7,066,904 B2 | 6/2006 | Rosenthal et al. |
| 7,087,061 B2 | 8/2006 | Chernenko et al. |
| 7,241,295 B2 | 7/2007 | Maguire |
| 7,309,324 B2 | 12/2007 | Hayes et al. |
| 7,389,148 B1 | 6/2008 | Morgan |
| 7,505,812 B1 | 3/2009 | Eggers et al. |
| 7,569,032 B2 | 8/2009 | Naimark et al. |
| 7,850,685 B2 | 12/2010 | Kunis et al. |
| 7,853,332 B2 | 12/2010 | Olsen et al. |
| 7,873,404 B1 | 1/2011 | Patton |
| 7,951,111 B2 | 5/2011 | Drasler et al. |
| 8,162,859 B2 | 4/2012 | Schultheiss et al. |
| 8,177,801 B2 | 5/2012 | Kallok et al. |
| 8,353,923 B2 | 1/2013 | Shturman |
| 8,556,813 B2 | 10/2013 | Cioanta et al. |
| 8,574,247 B2 | 11/2013 | Adams et al. |
| 8,728,091 B2 | 5/2014 | Hakala et al. |
| 8,747,416 B2 | 6/2014 | Hakala et al. |
| 8,888,788 B2 | 11/2014 | Hakala et al. |
| 8,956,371 B2 | 2/2015 | Hawkins et al. |
| 8,956,374 B2 | 2/2015 | Hawkins et al. |
| 9,005,216 B2 | 4/2015 | Hakala et al. |
| 9,011,462 B2 | 4/2015 | Adams et al. |
| 9,011,463 B2 | 4/2015 | Adams et al. |
| 9,044,618 B2 | 6/2015 | Hawkins et al. |
| 9,044,619 B2 | 6/2015 | Hawkins et al. |
| 9,072,534 B2 | 7/2015 | Hakala et al. |
| 9,138,249 B2 | 9/2015 | Adams et al. |
| 9,198,825 B2 | 12/2015 | Katragadda et al. |
| 9,333,000 B2 | 5/2016 | Hakala et al. |
| 9,421,025 B2 | 8/2016 | Hawkins et al. |
| 9,433,428 B2 | 9/2016 | Hakala et al. |
| 9,522,012 B2 | 12/2016 | Adams |
| 9,642,673 B2 | 5/2017 | Adams et al. |
| 9,993,292 B2 | 6/2018 | Adams et al. |
| 10,039,561 B2 | 8/2018 | Adams et al. |
| 10,118,015 B2 | 11/2018 | De La Rama et al. |
| 10,149,690 B2 | 12/2018 | Hawkins et al. |
| 10,154,799 B2 | 12/2018 | Van Der Weide et al. |
| 10,159,505 B2 | 12/2018 | Hakala et al. |

(56) References Cited

U.S. PATENT DOCUMENTS

| | | |
|---|---|---|
| 10,206,698 B2 | 2/2019 | Hakala et al. |
| 10,517,620 B2 | 12/2019 | Adams |
| 10,517,621 B1 | 12/2019 | Adams |
| 10,555,744 B2 | 2/2020 | Nguyen et al. |
| 10,682,178 B2 | 6/2020 | Adams et al. |
| 10,702,293 B2 | 7/2020 | Hawkins et al. |
| 10,709,462 B2 | 7/2020 | Nguyen et al. |
| 10,959,743 B2 | 3/2021 | Adams et al. |
| 10,973,538 B2 | 4/2021 | Hakala et al. |
| 11,000,299 B2 | 5/2021 | Hawkins et al. |
| 11,076,874 B2 | 8/2021 | Hakala et al. |
| 11,267,968 B2 | 3/2022 | Osswald et al. |
| 11,337,713 B2 | 5/2022 | Nguyen et al. |
| 11,432,834 B2 | 9/2022 | Adams |
| 11,534,187 B2 | 12/2022 | Bonutti |
| 11,596,424 B2 | 3/2023 | Hakala et al. |
| 11,622,780 B2 | 4/2023 | Nguyen et al. |
| 11,696,799 B2 | 7/2023 | Adams et al. |
| 11,771,449 B2 | 10/2023 | Adams et al. |
| 2001/0044596 A1 | 11/2001 | Jaafar |
| 2002/0045890 A1 | 4/2002 | Celliers et al. |
| 2002/0082553 A1 | 6/2002 | Duchamp |
| 2002/0177889 A1 | 11/2002 | Brisken et al. |
| 2003/0004434 A1 | 1/2003 | Greco et al. |
| 2003/0176873 A1 | 9/2003 | Chernenko et al. |
| 2003/0229370 A1 | 12/2003 | Miller |
| 2004/0006333 A1 | 1/2004 | Arnold et al. |
| 2004/0010249 A1 | 1/2004 | Truckai et al. |
| 2004/0044308 A1 | 3/2004 | Naimark et al. |
| 2004/0097963 A1 | 5/2004 | Seddon |
| 2004/0097996 A1 | 5/2004 | Rabiner et al. |
| 2004/0162508 A1 | 8/2004 | Uebelacker |
| 2004/0249401 A1 | 12/2004 | Rabiner et al. |
| 2004/0254570 A1 | 12/2004 | Hadjicostis et al. |
| 2005/0015953 A1 | 1/2005 | Keidar |
| 2005/0021013 A1 | 1/2005 | Visuri et al. |
| 2005/0059965 A1 | 3/2005 | Eberl et al. |
| 2005/0075662 A1 | 4/2005 | Pedersen et al. |
| 2005/0090888 A1 | 4/2005 | Hines et al. |
| 2005/0113722 A1 | 5/2005 | Schultheiss |
| 2005/0113822 A1 | 5/2005 | Fuimaono et al. |
| 2005/0171527 A1 | 8/2005 | Bhola |
| 2005/0228372 A1 | 10/2005 | Truckai et al. |
| 2005/0245866 A1 | 11/2005 | Azizi |
| 2005/0251131 A1 | 11/2005 | Lesh |
| 2006/0004286 A1 | 1/2006 | Chang et al. |
| 2006/0069424 A1 | 3/2006 | Acosta et al. |
| 2006/0074484 A1 | 4/2006 | Huber |
| 2006/0184076 A1 | 8/2006 | Gill et al. |
| 2006/0190022 A1* | 8/2006 | Beyar ............... A61F 2/958 606/192 |
| 2006/0221528 A1 | 10/2006 | Li et al. |
| 2007/0016112 A1 | 1/2007 | Schultheiss et al. |
| 2007/0088380 A1 | 4/2007 | Hirszowicz et al. |
| 2007/0129667 A1 | 6/2007 | Tiedtke et al. |
| 2007/0156129 A1 | 7/2007 | Kovalcheck |
| 2007/0239082 A1 | 10/2007 | Schultheiss et al. |
| 2007/0239253 A1 | 10/2007 | Jagger et al. |
| 2007/0244423 A1 | 10/2007 | Zumeris et al. |
| 2007/0250052 A1 | 10/2007 | Wham |
| 2007/0255270 A1 | 11/2007 | Carney |
| 2007/0282301 A1 | 12/2007 | Segalescu et al. |
| 2007/0299481 A1 | 12/2007 | Syed et al. |
| 2008/0097251 A1 | 4/2008 | Babaev |
| 2008/0188913 A1 | 8/2008 | Stone et al. |
| 2009/0041833 A1 | 2/2009 | Bettinger et al. |
| 2009/0227992 A1 | 9/2009 | Nir et al. |
| 2009/0230822 A1 | 9/2009 | Kushculey et al. |
| 2009/0247945 A1 | 10/2009 | Levit et al. |
| 2009/0254114 A1 | 10/2009 | Hirszowicz et al. |
| 2009/0299447 A1 | 12/2009 | Jensen et al. |
| 2010/0016862 A1 | 1/2010 | Hawkins et al. |
| 2010/0036294 A1 | 1/2010 | Hawkins et al. |
| 2010/0094209 A1 | 4/2010 | Drasler et al. |
| 2010/0114020 A1 | 5/2010 | Hawkins et al. |
| 2010/0114065 A1 | 5/2010 | Hawkins et al. |
| 2010/0121322 A1 | 5/2010 | Swanson |
| 2010/0160838 A1 | 6/2010 | Krespi |
| 2010/0179424 A1 | 7/2010 | Warnking et al. |
| 2010/0286709 A1 | 11/2010 | Diamant et al. |
| 2010/0305565 A1 | 12/2010 | Truckai et al. |
| 2011/0034832 A1 | 2/2011 | Cioanta et al. |
| 2011/0118634 A1 | 5/2011 | Golan |
| 2011/0208185 A1 | 8/2011 | Diamant et al. |
| 2011/0257523 A1 | 10/2011 | Hastings et al. |
| 2011/0295227 A1 | 12/2011 | Hawkins et al. |
| 2012/0071715 A1 | 3/2012 | Beyar et al. |
| 2012/0071889 A1 | 3/2012 | Mantell et al. |
| 2012/0095461 A1 | 4/2012 | Herscher et al. |
| 2012/0116289 A1 | 5/2012 | Hawkins et al. |
| 2012/0143177 A1 | 6/2012 | Avitall et al. |
| 2012/0157991 A1 | 6/2012 | Christian |
| 2012/0203255 A1 | 8/2012 | Hawkins et al. |
| 2012/0253358 A1 | 10/2012 | Golan et al. |
| 2013/0030431 A1 | 1/2013 | Adams |
| 2013/0041355 A1 | 2/2013 | Heeren et al. |
| 2013/0116714 A1 | 5/2013 | Adams et al. |
| 2013/0123694 A1 | 5/2013 | Subramaniyan et al. |
| 2013/0150874 A1 | 6/2013 | Kassab |
| 2013/0253622 A1 | 9/2013 | Hooven |
| 2014/0046229 A1 | 2/2014 | Hawkins et al. |
| 2014/0200443 A1 | 7/2014 | Chang et al. |
| 2014/0214061 A1 | 7/2014 | Adams et al. |
| 2015/0320432 A1 | 11/2015 | Adams |
| 2016/0151081 A1 | 6/2016 | Adams et al. |
| 2016/0324534 A1 | 11/2016 | Hawkins et al. |
| 2017/0135709 A1 | 5/2017 | Nguyen et al. |
| 2017/0311965 A1 | 11/2017 | Adams |
| 2021/0085347 A1 | 3/2021 | Phan et al. |
| 2021/0085383 A1 | 3/2021 | Vo et al. |
| 2021/0338258 A1 | 11/2021 | Hawkins et al. |
| 2022/0015785 A1 | 1/2022 | Hakala et al. |
| 2022/0152427 A1 | 5/2022 | Bonutti et al. |
| 2022/0240958 A1 | 8/2022 | Nguyen et al. |
| 2023/0043475 A1 | 2/2023 | Adams |
| 2023/0293197 A1 | 9/2023 | Nguyen et al. |
| 2023/0310073 A1 | 10/2023 | Adams et al. |
| 2023/0329731 A1 | 10/2023 | Hakala et al. |
| 2023/0380849 A1 | 11/2023 | Adams et al. |

FOREIGN PATENT DOCUMENTS

| | | |
|---|---|---|
| AU | 2013284490 B2 | 5/2018 |
| CN | 1204242 A | 1/1999 |
| CN | 1269708 A | 10/2000 |
| CN | 1942145 A | 4/2007 |
| CN | 101043914 A | 9/2007 |
| CN | 102057422 A | 5/2011 |
| CN | 102271748 A | 12/2011 |
| CN | 102355856 A | 2/2012 |
| CN | 102765785 A | 11/2012 |
| CN | 203564304 U | 4/2014 |
| CN | 114098898 A | 3/2022 |
| DE | 3038445 A1 | 5/1982 |
| DE | 623360 A1 | 11/1994 |
| DE | 202006014285 U1 | 12/2006 |
| EP | 0442199 A2 | 8/1991 |
| EP | 0571306 A1 | 11/1993 |
| EP | 0647435 A1 | 4/1995 |
| EP | 2253884 A1 | 11/2010 |
| EP | 2362798 B1 | 4/2014 |
| JP | S62-099210 U | 6/1987 |
| JP | S62-275446 A | 11/1987 |
| JP | H03-63059 A | 3/1991 |
| JP | H06-125915 A | 5/1994 |
| JP | H07-47135 A | 2/1995 |
| JP | H08-89511 A | 4/1996 |
| JP | H10-99444 A | 4/1998 |
| JP | H10-314177 A | 12/1998 |
| JP | H10-513379 A | 12/1998 |
| JP | 2002538932 A | 11/2002 |
| JP | 2004081374 A | 3/2004 |
| JP | 2004357792 A | 12/2004 |
| JP | 2005501597 A | 1/2005 |

(56) References Cited

FOREIGN PATENT DOCUMENTS

| | | | |
|---|---|---|---|
| JP | 2005095410 A | 4/2005 | |
| JP | 2005515825 A | 6/2005 | |
| JP | 2006516465 A | 7/2006 | |
| JP | 2007289707 A | 11/2007 | |
| JP | 2007532182 A | 11/2007 | |
| JP | 2008506447 A | 3/2008 | |
| JP | 2011513694 A | 4/2011 | |
| JP | 2011520248 A | 7/2011 | |
| JP | 2011524203 A | 9/2011 | |
| JP | 2011528963 A | 12/2011 | |
| JP | 2012505050 A | 3/2012 | |
| JP | 2012508042 A | 4/2012 | |
| JP | 2015525657 A | 9/2015 | |
| JP | 2015528327 A | 9/2015 | |
| JP | 6029828 B2 | 11/2016 | |
| JP | 6081510 B2 | 2/2017 | |
| WO | WO-1989011307 A1 | 11/1989 | |
| WO | WO-1996024297 A1 | 8/1996 | |
| WO | WO-1999000060 A1 | 1/1999 | |
| WO | WO-1999002096 A1 | 1/1999 | |
| WO | WO-2000056237 A2 | 9/2000 | |
| WO | WO-2004069072 A2 | 8/2004 | |
| WO | WO-2005099594 A1 | 10/2005 | |
| WO | WO-2005102199 A1 | 11/2005 | |
| WO | WO-2006006169 A2 | 1/2006 | |
| WO | WO-2006127158 A2 | 11/2006 | |
| WO | WO-2007088546 A2 | 8/2007 | |
| WO | WO-2007149905 A2 | 12/2007 | |
| WO | WO-2009121017 A1 | 10/2009 | |
| WO | WO-2009126544 A1 | 10/2009 | |
| WO | WO-2009136268 A1 | 11/2009 | |
| WO | WO-2009152352 A2 | 12/2009 | |
| WO | WO-2010014515 A2 | 2/2010 | |
| WO | WO-2010054048 A2 | 9/2010 | |
| WO | WO-2011006017 A1 | 1/2011 | |
| WO | WO-2011094111 A2 | 8/2011 | |
| WO | WO-2011143468 A2 | 11/2011 | |
| WO | WO-2012025833 A2 | 3/2012 | |
| WO | WO-2013059735 A1 | 4/2013 | |
| WO | WO-2014025397 A1 | 2/2014 | |
| WO | WO-2014025620 A1 | 2/2014 | |
| WO | WO-2015017499 A1 | 2/2015 | |
| WO | WO-2019099218 A1 | 5/2019 | |

OTHER PUBLICATIONS

U.S Unpublished U.S. Appl. No. 18/620,248, filed Mar. 28, 2024 titled "Drug Delivery Beyond the Blood-Brain Barrier Using Shock Waves," (Copy not submitted herewith pursuant to the waiver of 37 C.F.R. § 1.98(a)(2)(iii)).

International Search Report and Written Opinion received for International Application No. PCT/US2024/022272 mailed Jul. 15, 2024, 9 pages.

* cited by examiner

SHOCKWAVE CATHETERS FOR TREATING RHINOSINUSITIS

CROSS-REFERENCE TO RELATED APPLICATIONS

This application claims priority to and the benefit of U.S. Provisional Patent Application No. 63/456,272, filed Mar. 31, 2023, the entire contents of which are hereby incorporated by reference.

FIELD OF THE DISCLOSURE

The present disclosure relates generally to the field of medical devices and methods, and more specifically to catheter devices for treating narrowed regions in lumens of the ear or nose and methods of using such devices.

BACKGROUND

Chronic rhinosinusitis is a common condition characterized by chronic inflammation and/or infection of the nasal passages and sinuses. Rhinosinusitis can be caused by infection, allergy, mucosal hyperactivity, growths in the sinus, and/or anatomical problems that prevent proper drainage of the nasal passages and sinuses. Symptoms of rhinosinusitis can include nasal discharge or obstruction, facial congestion, pain or pressure around the eyes, cheeks, nose, or forehead, and reduced sense of smell and/or taste. When rhinosinusitis symptoms last twelve weeks or longer, a patient can be diagnosed with chronic rhinosinusitis.

Chronic rhinosinusitis can have a substantial negative impact on the quality of life of the patient. There are a variety of treatments for chronic rhinosinusitis. Corticosteroids, which may be delivered via an oral medication, nasal spray, or injection, can relieve inflammation; however, these steroids can cause serious side effects when used for long periods. While oral medications are widely available, such medications can require long periods before becoming effective and can have negative side effects. Nasal sprays and injections may offer more immediate effects; however, these methods suffer without proper patient compliance and can fail to reach the intended target area when that area is deep within the ear or sinus.

Surgical treatment options are also available for chronic rhinosinusitis. Endoscopic sinus surgery involves surgical resection to remove portions of the patient's anatomy to create drainage pathways. This may involve removing sinus polyps and/or removing normal anatomical features, such as portions of the ostiomeatal complex, in order to create drainage pathways. Another surgical treatment option available is balloon sinuplasty. In balloon sinuplasty, a catheter having a non-compliant inflatable balloon is inflated in a narrowed region to dilate a blocked sinus and then pressurized to pressures ranging from eight to eighteen atmospheres (8-18 atm). The energy stored in the balloon builds as the pressure increases, eventually breaking the bony structure in the patient's sinus to create sinus pathways. Balloon sinuplasty is gentler on anatomy than surgical resection and can better preserve mucociliary function in the sinus. However, the high pressures needed to enable the balloon to break bony structures in the sinus can damage soft tissues, such as the mucosa, and lengthen the healing period post-surgery. Moreover, if the inflation of the balloon failed to break the bony structure, an additional endoscopic surgery may be needed to successfully widen the blocked sinus.

SUMMARY

Disclosed herein are shock wave catheter devices for treating narrowed regions of lumens in the ear or nose of a patient and methods of using such devices. The shock wave catheter devices use shock waves to break the bony structure in the narrowed region to restore proper drainage, while minimizing damage to soft tissues. Moreover, the shock wave catheter devices can utilize low pressure compliant or semi-complaint balloons with directional shock wave emitters that enable the surgeon to selectively treat distinct areas of a narrowed region with location-specific shock waves. The peak pressure of such shock waves is greater relative to prior balloon sinuplasty methods, which enables the treatment of regions deeper within the tissue and may lead to longer term patency of the lumen.

In one aspect, disclosed herein is an exemplary method for treating a narrowed region of a lumen in the ear or nose of a patient. The method includes advancing a catheter within the lumen such that a distal end of the catheter is positioned proximate to the narrowed region. The distal end of the catheter includes at least one shock wave emitter that is surrounded by a fillable member. The method further includes filling the fillable member to expand the fillable member within the lumen. The method further includes generating at least one shock wave from the at least one shock wave emitter. The at least one shock wave creates one or more fractures in a bony structure of the narrowed region of the lumen that dilate the narrowed region.

In some aspects, the method includes irrigating the lumen to cause one or more bodily fluids to drain out of the lumen via the dilated narrowed region. In another aspect, the method includes adjusting a directionality of the at least one shock wave emitter prior to generating the one or more shock waves so that the at least one shock wave is directed toward the bony structure. In some aspects, adjusting the directionality of the at least one shock wave emitter includes rotating the catheter within the lumen about a center axis of the catheter. In other aspects, adjusting the directionality of the at least one shock wave emitter includes adjusting an external knob of the catheter to cause the catheter to rotate within the lumen about a center axis of the catheter. In further aspects, adjusting the directionality of the at least one shock wave emitter includes adjusting the catheter such that an external indicator is oriented along a desired direction. In another aspect, the fillable member includes a semi-compliant balloon or compliant balloon. In a further aspect, filling the fillable member includes pressurizing the fillable member to a pressure of less than 10 atm. In one aspect, filling the fillable member includes pressurizing the fillable member to a pressure of up to 6 atm. In some aspects, the method includes, after generating the at least one shock wave, increasing the diameter of the lumen in the ear or the nose of the patient by pressurizing the fillable member to a pressure of up to 10 atm. In some aspects, the method includes at least partially collapsing the fillable member; advancing the catheter further within the lumen such that the distal end of the catheter is positioned proximate to a different portion of the narrowed region or a further narrowed region; filling the fillable member to expand the fillable member within the lumen; and generating at least one shock wave from the at least one shock wave emitter, the at least one shock wave creating one or more fractures in the further narrowed region of the lumen to dilate the further narrowed region. In another aspect, advancing the catheter within the lumen includes advancing the catheter over a guidewire. In a further aspect, the lumen is part of a frontal sinus, a maxillary sinus, a sphenoid sinus, an ethmoid sinus, a sinus ostium, an inferior turbinate, a middle turbinate, a superior turbinate, a nasal cavity, the ostiomcatal complex, or a combination thereof. In yet a further aspect, the method includes locating the narrowed region using an imaging sensor of the catheter prior to generating the at least one shock wave. In some aspects, the method includes advancing an endoscope within the lumen such that a distal end of the endoscope is proximally offset from the distal end of the catheter; and obtaining one or more images of the distal end of the catheter to locate the narrowed region. In another aspect, the at least one shock wave delivers a therapeutically effective amount of an active agent of a drug to the lumen. In one aspect, the active agent can include a corticosteroid. In another aspect, the active agent comprises an antibiotic. In some aspects, a drug layer on the fillable member can include the active agent and one or more adjunctive agents.

In another aspect, disclosed herein is a device for treating a narrowed region of a lumen in the ear or nose of a patient. The device includes an elongated tube, at least one shock wave emitter, at least one imaging sensor, and a fillable member. The at least one shock wave emitter is configured to generate at least one shock wave along a working direction. The at least one imaging sensor is oriented to capture images along the working direction. The fillable member is sealed to a distal end of the elongated tube and surrounds the at least one shock wave emitter and the at least one imaging sensor. The fillable member is fillable with a conductive fluid. In some aspects, the fillable member includes a drug coating, and the least one shock wave delivers a therapeutically effective amount of an active agent of a drug to the lumen.

BRIEF DESCRIPTION OF THE FIGURES

Illustrative aspects of the present disclosure are described in detail below with reference to the following drawing figures. It is intended that the embodiments and figures disclosed herein are to be considered illustrative rather than restrictive.

DETAILED DESCRIPTION

Figure 1:
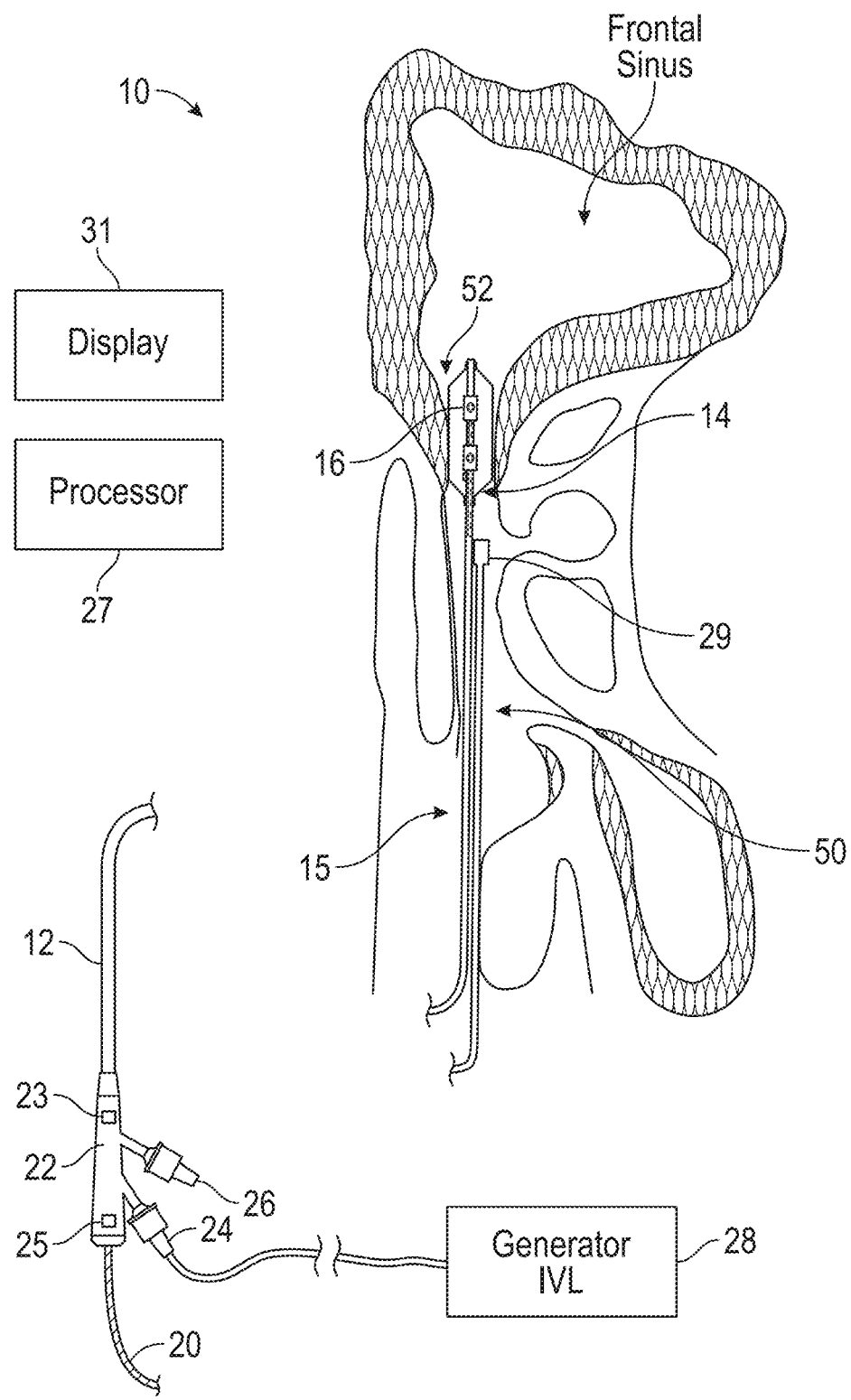
FIG. 1 illustrates a system comprising an exemplary shock wave catheter device being used to treat a narrowed region in a body lumen, according to one or more aspects of the present disclosure.

The following description is presented to enable a person of ordinary skill in the art to make and use the various embodiments disclosed herein. Descriptions of specific devices, assemblies, techniques, and applications are provided only as examples. Various modifications to the examples described herein will be readily apparent to those of ordinary skill in the art, and the general principles described herein may be applied to other examples and applications without departing from the spirit and scope of the various embodiments. Thus, the various embodiments are not intended to be limited to the examples described herein and shown, but rather are to be accorded the scope consistent with the claims.

Described herein are shock wave catheter devices for treating narrowed regions of lumens in the ear or nose of a patient and methods of using such devices. The catheter device can include at least one shock wave emitter having at least one pair of electrodes that are configured to generate one or more shock waves. As used herein, the term "electrode" refers to an electrically conducting element (typically made of metal) that receives electrical current and subsequently releases the electrical current to another electrically conducting element. In the context of the present disclosure, electrodes are often positioned adjacent to each other, such as in an arrangement of an inner electrode and an outer electrode. Accordingly, as used herein, the term "electrode pair" refers to two electrodes that are positioned adjacent to each other such that application of a sufficiently high voltage to the electrode pair will cause an electrical current to transmit across the gap (also referred to as a "spark gap") between the two electrodes (e.g., from an inner electrode to an outer electrode, or vice versa, optionally with the electricity passing through a conductive fluid or gas therebetween). In some contexts, one or more electrode pairs (positioned across one or more emitters) may also be referred to as an electrode assembly. In the context of the present disclosure, the term "emitter" broadly refers to the region of an electrode assembly where the current travels across the electrode pair, generating a shock wave. The term "emitter band" refers to a band of conductive material that may form one or more electrodes of one or more electrode pairs, thereby forming a location of one or more emitters.

The catheter device can be advanced within a body lumen of a patient such that a distal portion of the catheter device having the shock wave emitter(s) is positioned proximate to a narrowed region of the body lumen to be treated. Voltage can then be supplied to the shock wave emitter(s) to create one or more shock waves that propagate outwardly and impinge upon the narrowed region. As the shock waves impinge upon the narrowed region, the shock waves can create one or more fractures in the bony structure of the narrowed region, which dilate the narrowed region. Accordingly, the catheter device can be used to relieve symptoms caused by narrowed regions, such as narrowed regions in lumens of the ear and/or nose.

In one or more examples, the shock wave emitter(s) of the catheter device can be configured to generate shock waves that are directed in a specific direction. During treatment, the orientation of the shock wave emitter(s) can be adjusted such that shock waves are directed to a specific region of the patient's lumen. Thus, shock waves can be generated that target a specific region without adversely affecting nearby regions. Treating a region of a patient's lumen may involve utilizing image data from one or more image sensors. For example, the catheter device can include an image sensor that captures image data of a working area that corresponds with the area that the shock wave emitter(s) are directed towards. Accordingly, the orientation of the shock wave emitter(s) can be adjusted based on image data from such sensors to ensure that a particular region will be impacted by the shock waves and/or to target a new region for a subsequent shock wave treatment.

In one or more examples, the catheter device can include a fillable member (e.g., a balloon), that expands around the shock wave emitters to surround the emitters with a conductive fluid. This conductive fluid can enable the generation of shock waves and can propagate the shock waves into the lumen of the body. During treatment, the fillable member can be pressurized to a pressure of less than ten atmospheres (10 atm), which is relatively gentler on the patient's anatomy than a higher-pressure balloon, such as those used in balloon sinuplasty. For instance, during treatment, the fillable member may be pressurized to a pressure of approximately four atmospheres (4 atm) or a pressure of approximately 6 atmospheres (6 atm). In some examples, after a treatment, the fillable member can be pressurized to a pressure of up to ten atmospheres (10 atm).

In one or more examples, the fillable member may have an external drug coating. The external drug coating can be releasable from the surface of the fillable member by the shock waves, such that the shock waves generated by the shock wave emitter(s) deliver a therapeutically effective amount of an active agent of a drug to the patient's lumen during treatment. Delivering an active agent of a drug to the lumen via one or more shock waves may beneficially cause the agent to penetrate deeper into the tissues than other drug application methods, such as a nasal spray or oral medication. The drug coating may be in a crystalline form, an amorphous form, or combination thereof on the surface of the fillable member. U.S. patent application Ser. No. 18/620, 248, the contents of which are incorporated herein in its entirety, describes an example of using shock waves to evade the blood-brain barrier (BBB) and deliver a drug coated on the surface of a fillable member of a shock wave catheter to the central nervous system (CNS).

As provided herein, it should be appreciated that any disclosure of a numerical range describing dimensions or measurements such as thicknesses, length, weight, time, frequency, temperature, voltage, current, angle, etc. is inclusive of any numerical increment or gradations within the ranges set forth relative to the given dimension or measurement. Furthermore, numerical designators such as "first", "second", "third", "fourth", etc. are merely descriptive and do not indicate a relative order, location, or identity of elements or features described by the designators. For instance, a "first" shock wave may be immediately succeeded by a "third" shock wave, which is then succeeded by a "second" shock wave. As another example, a "third" emitter may be used to generate a "first" shock wave and vice versa. Accordingly, numerical designators of various elements and features are not intended to limit the disclosure and may be modified and interchanged without departing from the subject invention.

In some embodiments, a catheter as disclosed herein is a so-called "rapid exchange-type" ("Rx") catheter provided with an opening portion through which a guide wire is guided (e.g., through a middle portion of a central tube in a longitudinal direction). In other embodiments, a catheter may be an "over-the-wire-type" ("OTW") catheter in which a guide wire lumen is formed throughout the overall length of the catheter, and a guide wire is guided through the proximal end of a hub.

FIG. 1 illustrates a system 10 comprising an exemplary shock wave catheter device 15 being used to treat a narrowed region 52 in a body lumen 50, according to one or more aspects of the present disclosure. The catheter device 15 includes a catheter body 12 that extends between the proximal end 22 and the distal end 14 of the catheter device 15. The catheter device 15 can be introduced into a narrowed region in a lumen, such as the narrowed region 52 of the frontal sinus as depicted in FIG. 1, and then used to dilate the narrowed region 52 using one or more shock waves generated from the distal end 14 of the catheter device 15.

The distal end 14 of the catheter device 15 can include a fluid fillable member, such as a compliant or semi-compliant balloon, which surrounds at least one shock wave emitter 16 that is configured to generate a one or more shock waves for breaking bony structures in the body lumen 50. The bony structures that can be broken by the pressure of shock waves can include structures that include hard tissues (e.g., cartilage and/or rigid osseous tissue), such as the turbinates within the nose.

The shock wave emitter 16 includes one or more emitters that emit shock waves that propagate outwardly from the emitter. An emitter may include any suitable combination of electrodes that form a pair of electrodes separated by a fluid filled gap. A suitable voltage applied across the gap causes a plasma arc to form, which causes the expansion and collapse of a cavitation bubble, thus creating a shock wave. An emitter can include one or more insulated wires having exposed portions (e.g., an insulated wire having an exposed region where the insulation has been removed) and/or one or more conductive emitter bands (e.g., conductive metal sheaths) mounted around the catheter body 12.

The proximal end 22 of the catheter device 15 remains outside of the body lumen 50 of the patient during treatment. The proximal end 22 can include a handle for grasping by a surgeon. The proximal end 22 can include a fluid port 26 for filling and evacuating the fillable member of the catheter device 15 with conductive fluid, such as saline. In one or more examples, the conductive fluid may also contain an x-ray contrast fluid to permit fluoroscopic viewing of the catheter by a surgeon during use. The proximal end 22 can include an electrical connection port 24 that provides an electrical connection between the shock wave emitter 16 and an external high voltage pulse generator 28, such as the generator shown in FIG. 1. In one or more examples, the proximal end 22 may include an entry port for receiving a removable guidewire 20, which can aid in the insertion placement of the catheter device 15 into a body lumen during treatment. The guidewire 20 may include one or more imaging sensors connected to an imaging processor and/or display that enables the surgeon to visually locate the region to be treated. Additionally or alternatively, the guidewire 20 and/or other regions of the catheter device 15 can include navigation sensors (e.g., radiofrequency sensors, electromagnetic sensors, etc.) that operate in conjunction with a tracking system and software that indicate the position of the guidewire and/or catheter within a body lumen on a visual display.

The catheter body 12 can include a flexible hollow shaft or elongated tube and may include internal conduits connecting elements of the distal end 14 with elements of the proximal end 22. For instance, the catheter body 12 can include one or more wire lumens for carrying one or more insulated wires extending from the high voltage pulse generator 28 to the shock wave emitter(s) 16. The catheter body 12 may include one or more fluid lumens such as a fluid inlet lumen and a fluid outlet lumen, for carrying conductive fluid from the fluid port 26 to the distal end 14 of the catheter device 15. The catheter body 12 may include a guide wire lumen sized to receive the guidewire 20. In one or more examples, the catheter body 12 has compliant material properties such that the catheter device 15 can be torqued, curved, and physically manipulated to maneuver the catheter device 15 to the treatment region within the body lumen.

The high voltage pulse generator 28 can be used to control the magnitude of shock waves generated via the shock wave emitter(s) 16. For instance, one or more of the magnitude, current, frequency, and/or duty cycle of the voltage pulse that is applied across the electrodes of a shock wave emitter 16 can be varied to adjust the magnitude of the shock waves generated. Although shock wave devices described herein generate shock waves based on high voltage applied to electrodes, it should be understood that a shock wave device additionally or alternatively may comprise a laser and optical fibers as a shock wave emitter system whereby the laser source delivers energy through an optical fiber and into a fluid to form shock waves and/or cavitation bubbles.

The catheter device 15 can include at least one image sensor and/or at least one navigation sensor (not shown in figure), which can be connected to an imaging processor, such as processor 27, and/or an external display, such as display 31. The processor 27 can process data captured by the image sensor(s) or transmitted by the navigation sensor(s) in order to display one or more images or renderings on the display 31 during a shock wave treatment. These images and/or renderings may be used to position the distal end 14 of the catheter device 15 in a narrowed region before generating shock waves and/or to orient the distal end 14 of the catheter device 15, such as to orient the distal end 14 such that the shock waves generated will be propagated in a particular direction.

In one or more examples, the proximal end 22 of the catheter device 15 can include a control knob 23 and/or an indicator 25, which can be used to adjust the directionality of the distal end 14 of the catheter device 15. The control knob 23 can be used by a surgeon to rotate the distal end 14 of the catheter device 15 within the patient's lumen. For example, a surgeon can rotate the control knob 23 counterclockwise to cause the catheter device 15 to rotate accordingly. The indicator 25 can represent the direction that the shock wave emitter(s) 16 of the distal end 14 are facing (e.g., the direction that shock waves will travel when propagating outwardly from the shock wave emitter(s) 16). Accordingly, the surgeon can utilize the control knob 23 and/or indicator 25 to orient the distal end 14 to cause shock waves to impinge on a particular region of the patient's lumen. The control knob 23 or other user control can be used for steering the distal end 14 of the catheter device 15, which may be configured to bend relative to a proximal portion of the catheter body 12. The ability to steer the distal end 14 of the catheter device 15 can be useful for locating the distal end 14 of the catheter device 15 adjacent to a target treatment region in large body lumens. For example, for a relatively large body lumen such as the frontal sinus shown in FIG. 1, the distal end 14 of the catheter device 15 may be steered within the frontal sinus so that the shock wave emitter(s) 16 are positioned adjacent to (or a desired distance from) a target treatment region of the frontal sinus.

In one or more examples, the system 10 can include an imager, such as an endoscopic imager 29, which can be used to position and/or orient the distal end 14 in the lumen. For example, the endoscopic imager 29 may be advanced within the lumen and obtain imaging data of the distal end 14 of the catheter device 15 within the lumen, which can be used by a surgeon to locate a narrowed region to be treated and/or to monitor treatment of the lumen while generating shock waves. When both the endoscopic imager 29 and catheter device 15 are advanced within a patient's lumen, the distal end of the endoscopic imager 29 may be positioned such that it is proximally offset from the distal end 14 of the catheter device 15 (as shown in FIG. 1). Such configuration may allow the endoscopic imager 29 to capture imaging data of the distal end 14 of the catheter device 15.

Figure 2C:
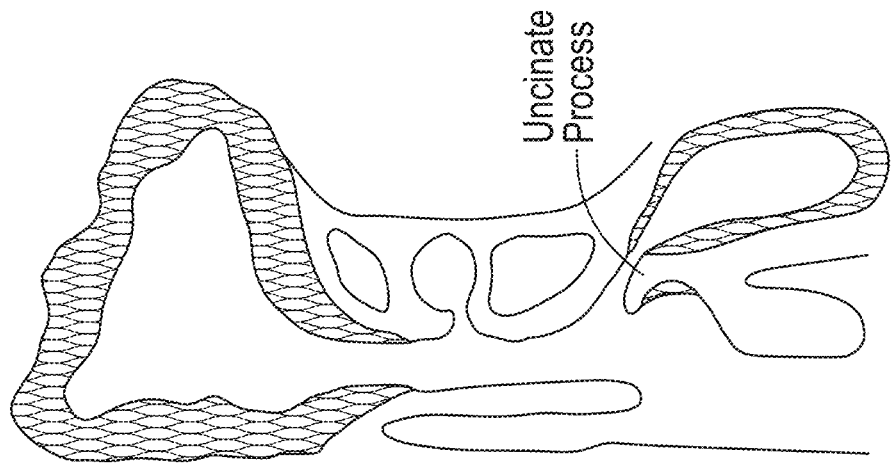
FIG. 2A-2C depict a shock wave catheter device being used to treat excess mucus in the frontal sinus of a patient, according to one or more aspects of the present disclosure.
Figure 2B:
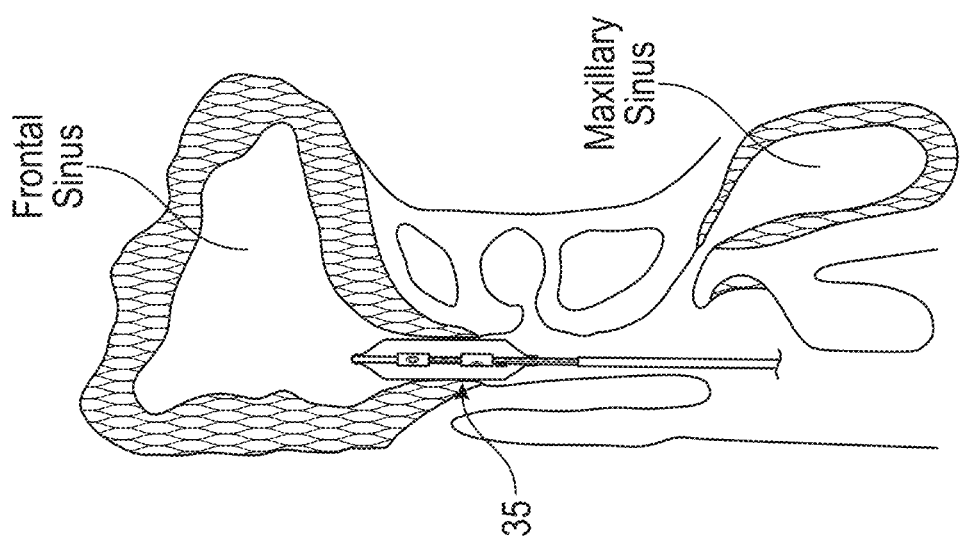
Figure 2A:
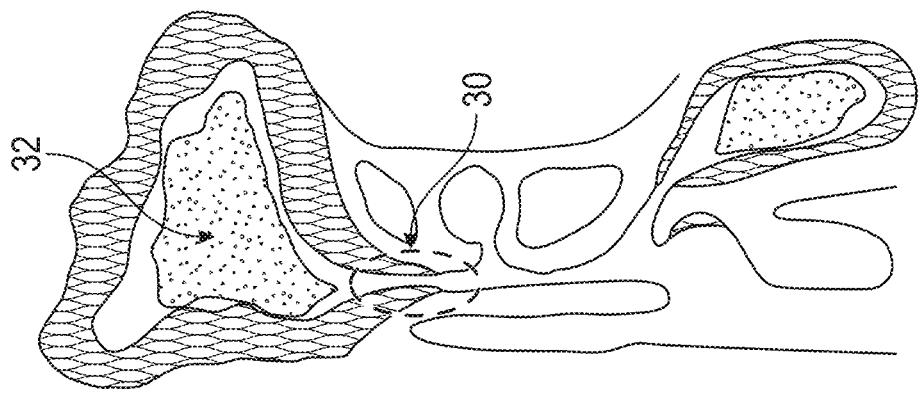

The system 10 can be used to dilate narrowed regions in lumens of the ear or nose of a patient. For example, FIG. 2A-2C depict a shock wave catheter system being used to treat excess mucus in the frontal sinus of a patient. In particular, FIG. 2A depicts the frontal sinus of a patient with excess mucus 32 in the frontal sinus and the maxillary sinus. Such buildup may be ameliorated by dilating the treatment region 30 such that the excess mucus 32 can drain through the patient's sinus passages. To do so, a catheter device 35, such as the catheter device 15 of FIG. 1, can be advanced within the patient's sinus such that the catheter device 35 is located in the treatment region 30, as shown in FIG. 2B. A fillable member of the catheter device 35 can then be filled with a conductive fluid to expand the fillable member within the treatment region 30. The catheter device 35 can then be used to generate one or more shock waves that propagate outwardly. As the shock waves propagate outwardly, they can impact the bony structure of the patient's sinus to generate small fractures in the bony structure that dilate the treatment region 30. When the catheter device 35 is removed, as shown in FIG. 2C, the treatment region 30 can remain in the dilated position, thereby permitting the excess mucus 32 to drain. Optionally, where mucous is located at the treatment region 30 (e.g., covering the treatment region), expansion of the fillable member may push at least some of the mucous out of the way of the catheter device 35 and treatment region 30 so that shock waves do not travel through the mucous (or through as much of the mucous) to reach the treatment region 30. In at least some instances, expansion of the fillable member may be sufficient to push mucous completely out of the way such that the fillable member is in contact with at least a portion of the tissue of the treatment region 30. Pushing mucous out of the way of the catheter device 35 and treatment region 30 may increase the effectiveness of the treatment since there is less (or no) mucous to dissipate energy of the shock waves.

Figure 3A:
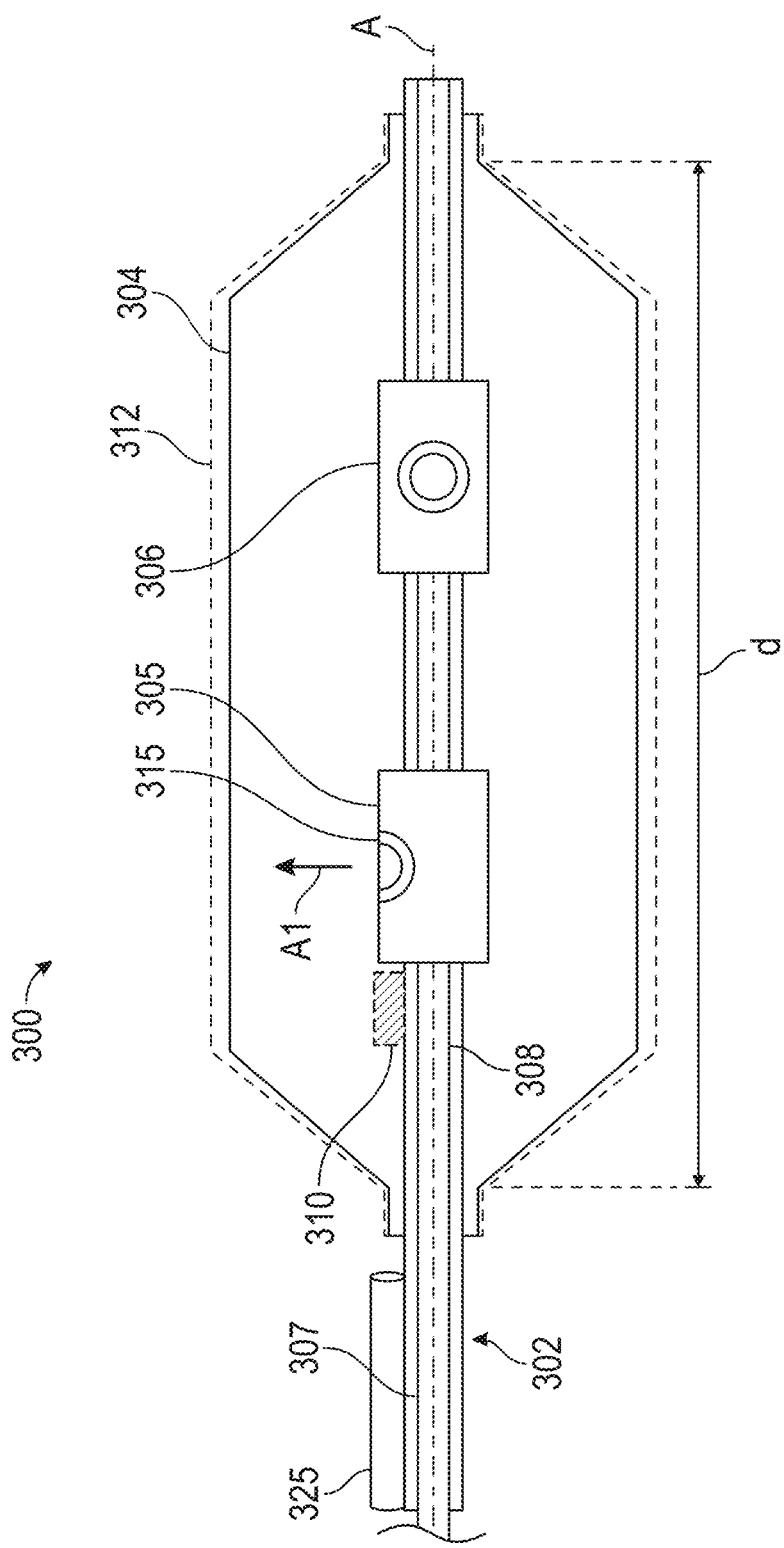
FIG. 3A and FIG. 3B illustrate a side view of the distal end of an exemplary shock wave catheter device for treating a narrowed region of a patient's ear or nose, according to one or more aspects of the present disclosure.
Figure 3B:
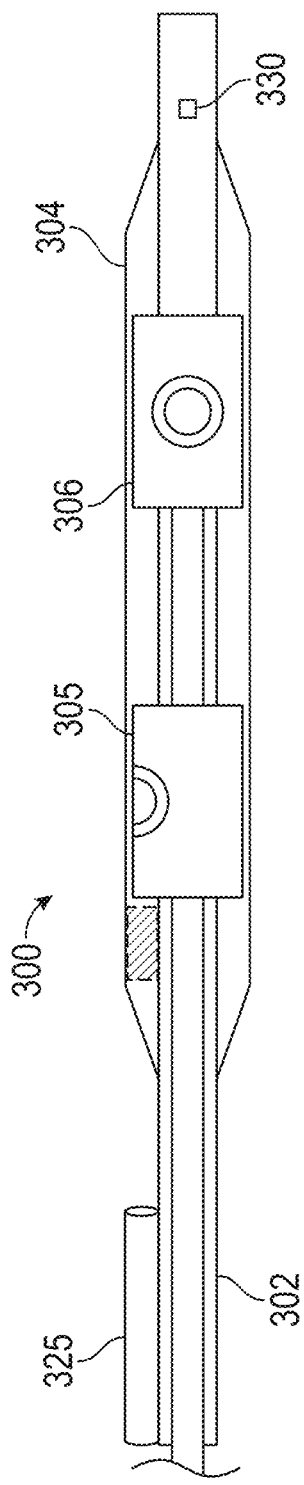

FIGS. 3A and 3B illustrate a side view of the distal end of an exemplary shock wave catheter device 300 for treating a narrowed region of a patient's ear or nose, according to one or more aspects of the present disclosure. The catheter device 300 can be used in a system for treating narrowed regions in the patient's ear or nose, such as the system 100 of FIG. 1. The catheter device 300 includes a fillable member 304 that is sealed to an elongated tube 302 (FIG. 3A shows the fillable member 304 in a filled state and FIG. 3B shows the fillable member 304 in an unfilled state). Within the fillable member 304, the catheter device 300 includes pair of emitter assemblies 305, 306 that are connected to the distal end of at least one wire (not shown in figure). The catheter device 300 also includes an irrigation lumen 325 and an image sensor 310.

Figure 3C:
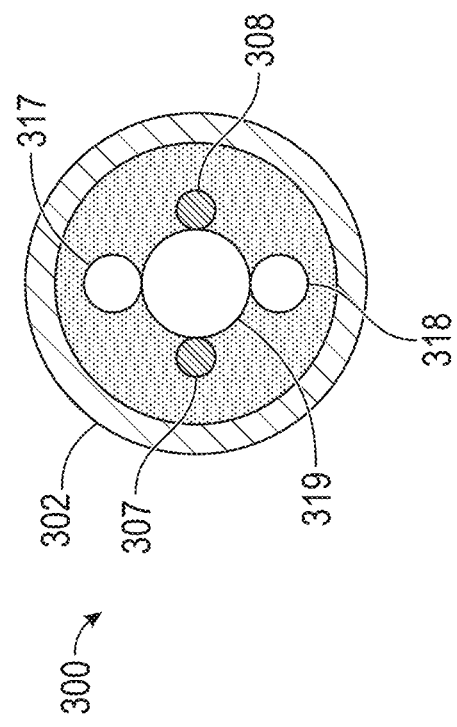
FIG. 3C illustrates a cross-sectional view of the elongated tube of the catheter device of FIGS. 3A and 3B, according to one or more aspects of the present disclosure.

As noted above, the elongated tube 302 can include one or more internal conduits connecting elements of the distal end of the catheter device 300 to external elements such as a voltage source and/or a fluid source. An example of such internal conduits is shown more clearly in FIG. 3C, which illustrates a cross-sectional view of the elongated tube 302 of FIGS. 3A and 3B. Within the elongated tube 302 are two wires 307 and 308, two fluid lumens 317 and 318, and a guidewire lumen 319. The proximal ends of the wires 307 and 308 can be connected to a pulsed voltage source, such as the high voltage pulse generator 28 of FIG. 1, such that the wires 307 and 308 can deliver voltage to the shock wave emitter assemblies 305, 306. The guidewire lumen 319 can receive a guidewire for positioning the catheter device 300, such as the guidewire 20 of FIG. 1. The fluid lumens 317 and 318 can carry conductive fluid to the distal end of the catheter device 300, which can be used to fill the fillable member 304.

The shock wave emitter assemblies 305, 306 can be configured such that a shock wave is generated in response to voltage pulse being delivered via at least one wire 307, 308. For example, when voltage is applied to shock wave emitter assembly 305 and/or 306, which each have at least one electrode pair having electrodes that are separated apart from one another by a gap and surrounded by conductive fluid, small gas bubbles are created around the electrodes that insulate the electrodes. Subsequently, a plasma arc forms across the gap between the electrodes of the electrode pair, thereby creating a low impedance path were current flows freely. The heat from the plasma arc heats the conductive fluid to create a rapidly expanding vapor bubble. The expansion and collapse of the vapor bubble creates a shock wave that propagates outwardly from the shock wave emitter.

One or more of the shock wave emitter assemblies 305, 306 can be configured to generate shock waves that propagate outwardly in a specific direction. For instance, in the example shown in FIG. 3A, the shock wave emitter assembly 305 includes an electrode pair 315 configured to generate shock waves that radiate outwardly in the direction indicated by the arrow A1 (e.g., upward with respect to the orientation depicted). In contrast, the shock wave emitter 306 includes an electrode pair 315 that is configured to generate shock waves that radiate outwardly along a direction that is circumferentially offset by 90 degrees relative to the arrow A1 (e.g., orthogonal or "out of the page").

As shock waves radiate outwardly, pressure from the shock waves impinge upon surrounding tissues within the body lumen, and the pressure of a given shock wave may radiate in a multitude of directions. Nonetheless, the specific direction that a shock wave emitter is oriented along (e.g., for the shock wave emitter assembly 305, the direction of the arrow A1) can correspond with the highest amplitude portion of the shock wave(s). For instance, although shock waves emitted from the shock wave emitter assembly 305 may generally propagate along the direction indicated by the arrow A1 with some deviation in other directions, the highest amplitude portion of those shock waves can nonetheless propagate in the direction of the arrow A1.

Figure 3D:
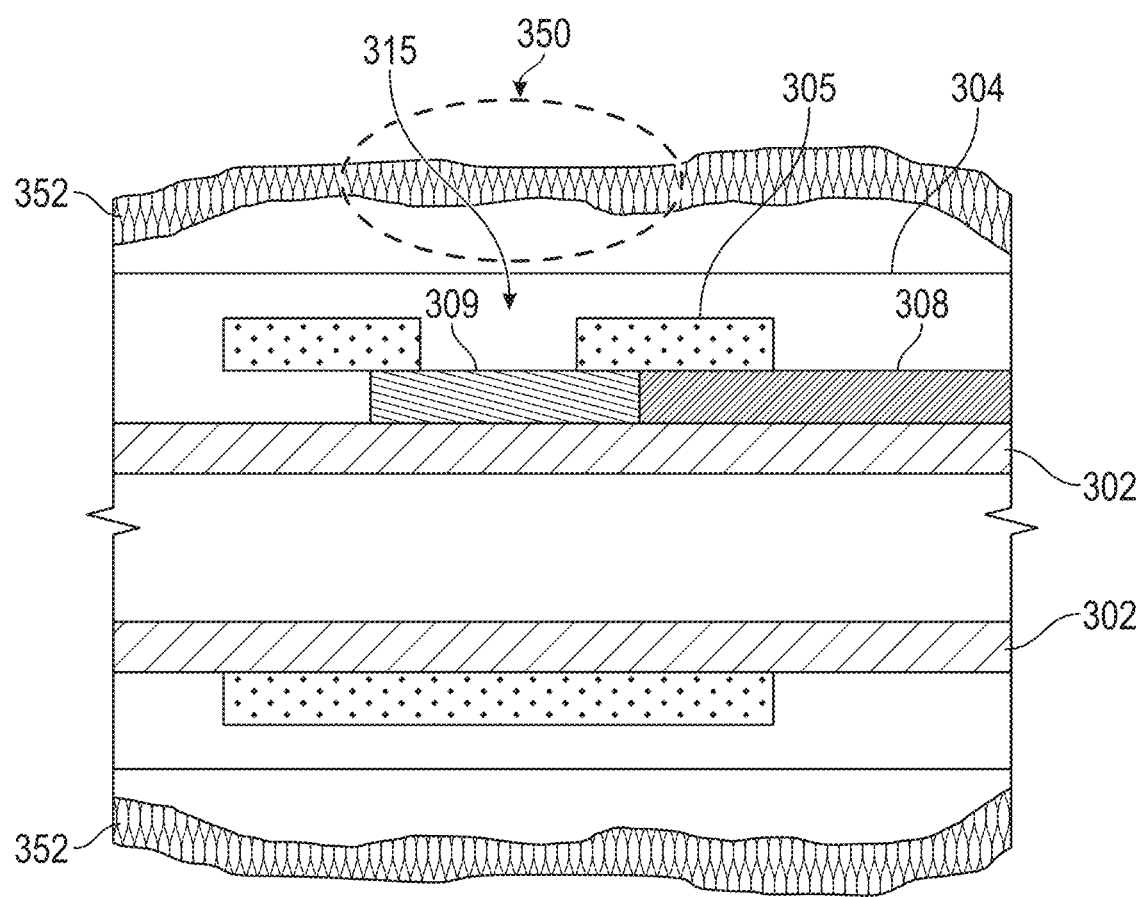
FIG. 3D illustrates a cross-sectional view depicting the directionality of an emitter of the catheter device of FIGS. 3A and 3B, according to one or more aspects of the present disclosure.

FIG. 3D illustrates a cross-sectional view depicting the directionality of the emitter assembly 305 of the catheter device 300 of FIGS. 3A and 3B, according to one or more aspects of the present disclosure. The emitter assembly 305 is depicted located within a patient's body lumen 352. The electrode pair 315 includes the emitter assembly 305 and the distal end 309 of the wire 308. When voltage is supplied to the wire 308, current can travel across the gap between the distal end 309 of the wire 308 and the emitter assembly 305 to generate one or more shock waves. The shock wave(s) will propagate towards the treatment region 350 of the body lumen 352. That is, the emitter assembly 305 is configured such that at least the highest amplitude portion of the shock waves propagates toward the treatment region 350. In particular, the opposite side of the body lumen 352 is not impacted by shock waves propagating towards the treatment region 350. Accordingly, the catheter device 300 can be used to treat specific regions of a patient's body lumen while leaving other regions untreated. This may be useful, for example, if a surgeon wants to treat one side of a patient's body lumen and/or does not want to treat a certain region of the patient's body lumen. As shown in this illustration, the surgeon could generate shock waves that impinge upon the treatment region 350 but does not impinge on the opposing side of the body lumen. In the context of sinus anatomy, the treatment region 350 can be bony structures underlying the tissue of the frontal, ethmoid, maxillary, or sphenoid sinuses, while the body lumen 352 can be the nasal septum. Conversely, if applied for septoplasty, shock waves may be directed at a nasal septum to aid in preparing the nasal septum for trimming, repositioning, and/or replacing that anatomy.

The distal end of the catheter device 300 can be rigid such that the directionality of the shock wave emitters can be adjusted by rotating the catheter device 300 about a center axis A of the catheter device 300. In one or more examples, the proximal end of the catheter device 300 can include a knob, such as the control knob 23 of FIG. 1, which can be used to rotate the distal end of the catheter device 300. The proximal end of the catheter device 300 may also include a directional indicator, such as the indicator 25 of FIG. 1, which a surgeon may use to adjust the directionality of the shock wave emitters. For example, the surgeon can adjust the proximal end of the catheter device 300 such that the directional indicator is oriented along a desired direction. In some examples, the user can simply rotate the entire device via the handle to change the directionality of the shock wave emitter.

Returning to FIG. 3A, the catheter device 300 includes a pair of shock wave emitter assemblies 305, 306. However, this is provided for example only, and the catheter device 300 may include a single shock wave emitter or more than two shock wave emitters, such as three shock wave emitters, four shock wave emitters, five shock wave emitters, six shock wave emitters, etc. Where the catheter device 300 includes multiple shock wave emitters, the shock wave emitters may be configured to generate shock waves that propagate outwardly in the same direction, or to generate shock waves that propagate outwardly in different directions (e.g., as shown with respect to the shock wave emitter assembly 305 and the shock wave emitter 306).

When the catheter device 300 includes multiple shock wave emitters, the shock wave emitters may be located closely longitudinally adjacent to one another such that the shock waves generated by the shock wave emitters constructively interfere with one another, as described in U.S. application Ser. No. 16/967,544, which is hereby incorporated by reference. Moreover, the shock wave emitter assemblies 305, 306 can include a single electrode pair or multiple electrode pairs. As described in the above reference, when a shock wave emitter includes multiple electrode pairs, those electrode pairs may be closely circumferentially adjacent to one another such that the shock waves generated at the electrode pairs constructively interfere with one another. For instance, the shock wave emitter assembly 305 can include multiple electrode pairs that are circumferentially offset from one another along the emitter. Further details and implementations of such electrodes, electrodes assemblies, and emitters are disclosed in U.S. Pat. Nos. 8,888,788, and 10,709,462 and U.S. Publication No. 2021/0085347, each of which is hereby incorporated by reference.

The fillable member 304 can be a flexible member, such as a compliant or semi-compliant balloon, which is configured to at least partially expand in response to being filled by a conductive fluid, such as water or saline. The fillable member 304 can be formed from any suitable material that enables the member to stretch or shrink as the fluid pressure within the member changes (e.g., in response to filling the member with fluid or evacuating such fluid). For example, the fillable member 304 can be formed from an elastic material such as nylon, polyamide, polyurethane, etc. In one or more examples, the fillable member 304 may be formed of a material that does not undergo elastic stretching or shrinking as the fluid pressure within the member changes, such as a material suitable for a non-compliant balloon. The fillable member 304 may include multiple layers, which may include any combination of such materials, such as an inner layer of polyamide and outer layer of nylon. The fillable member 304 can include a working length, corresponding to the distance d extending between tapered regions of the member. In one or more examples, the working length can be between ten and seventy millimeters (10-70 mm), or greater than seventy millimeters (70 mm).

The fillable member 304 is depicted in FIG. 3B with the fillable member in an unfilled state. As shown, relative to the filled version of FIG. 3A, the fillable member in the unfilled state has a smaller diameter. In one or more examples, the diameter of the fillable member 304 after being filled with conductive fluid may be between three and forty millimeters (3-40 mm), or greater than forty millimeters (40 mm). A diameter of the fillable member 304 when fully filled may be between about 3-40 mm, 10-40 mm, 20-40 mm, and any increments and gradations of diameters within these ranges. Variations of the fillable member 304 can be sized according to the target anatomy of the patient. For example, a catheter device 300 having a larger fillable member 304 can be used for a larger body lumen and a catheter device 300 having a smaller fillable member 304 can be used for a smaller body lumen. Similarly, a length of the fillable member 304 may be different for different target anatomy. Exemplary ranges of length of the fillable member 304 include about 10-1000 mm, about 10-500 mm, about 20-100 mm, and any increments and gradations of lengths within these ranges. A physician may access to a number of different variations of the catheter device 300 having different sizes and may selected a variation with a suitable combination of dimensions (e.g., diameter and length) of the fillable member 304 based on characteristics of the patient, such as age, gender, disease, anatomical restrictions, etc.

The catheter device 300 can include one or more lumens (such as the fluid lumens 317 and 318 of FIG. 3C) for filling the fillable member 304, such as an inlet lumen and an outlet lumen, or one single fluid lumen. Evacuating fluid from the fillable member 304 may be referred to as collapsing the fillable member 304, which may involve completely collapsing or at least partially collapsing the fillable member 304. Alternatively, if the fillable member 304 does not undergo elastic stretching or shrinking, evacuating the fillable member 304 may involve removing fluid within the fillable member 304 without an appreciable change in the diameter of the member.

The fillable member 304 may include an external drug coating 312. The external drug coating 312 may be releasable from the member by the shock waves, such that as the shock waves generated by the shock wave emitter 306 delivers a therapeutically effective amount of an active agent of a drug to the lumen during treatment. Delivering an active agent of a drug (in crystalline or amorphous form, or a combination thereof) to the lumen via one or more shock waves may beneficially cause the agent to penetrate deeper into the tissues than other drug application methods, such as a nasal spray or oral medication.

The external drug coating 312 may include a plurality of microspheres or microcapsules of an active agent, or a layer of an active agent that is bonded to the outer surface of the fillable member 304. The active agent can comprise a corticosteroid, such as prednisolone, methylprednisolone, beclomethasone dipropionate, triamcinolone acetonide, flunisolide, budesonide, fluticasone propionate, mometasone furoate, ciclesonide, fluticasone furoate, betamethasone sodium phosphate, or any combination thereof. The active agent can comprise an antibiotic, such as amoxicillin/clavulanic acid, co-trimoxazole, fluoroquinolone, ciprofloxacin, cefuroxime axetil, roxithromycin, quinolone, or any combination thereof. In one or more examples, the external drug coating 312 may comprise one or more adjunctive agents, such as antimycotics, anti-immunoglobulin E (anti-IgE), anti-interleukin-5 (anti-IL5), antihistamines, aspirin, bacterial lysates, capsaicin, decongestants, furosemide, immunosuppressants, leukotriene antagonists, nasal irrigation agents, mucolytic agents, probiotics, proton pump inhibitors, reslizumab, mepolizumab, or any combination thereof.

The catheter device 300 may include an irrigation lumen 325, which can be used to flush the patient's lumen during treatment. For instance, after dilating a narrowed region of a lumen, irrigation fluid (such as saline or water) may be introduced into the lumen to encourage any excess mucus remaining in the lumen to drain via the dilated region of the lumen. In one or more examples, the fillable member 304 may be at least partially collapsed before introducing irrigation fluid via the irrigation lumen 325. Alternatively, the fillable member 304 may remain filled while irrigation fluid is introduced.

In one or more examples, the catheter device 300 can include at least one image sensor 310, which can be connected to an external image processing device and/or display, such as the processor 27 and/or display 31 of FIG. 1. The image sensor 310 can be located adjacent to a shock wave emitter 306 and may be configured to obtain image data of a working area where shock waves propagate outwardly from the shock wave emitter 306. For instance, as discussed above, one or more shock wave emitters 306 can be configured to propagate shock waves along a particular direction (e.g., a working direction), and the image sensor 310 can be configured to capture image data of the region within the lumen along that direction. The image data from the image sensor 310 can be used for positioning the catheter device 300 adjacent to a narrowed region within a lumen such that shock waves generated from the shock wave emitter(s) 306 impinge on an area of the narrowed region having a bony structure that can be fractured in order to dilate the narrowed region.

In one or more examples, the distal end of the catheter device 300 may include one or more location sensors 330. The location sensor 330 can provide location data to one or more external sensors or receivers (e.g., as part of a navigation system). Data from the location sensor 330 and the one or more external sensors can be provided to an external processor (such as the processor 27 of FIG. 1), which can track the movement of the distal end of the catheter device 300 within the patient's lumen. For instance, the surgeon may perform a pre-treatment mapping procedure (e.g., a calibration procedure) to map the patient's anatomy in the lumens of the ear and/or nose, and then utilize the map and the location data during treatment to monitor movement of the catheter device 300.

Figure 4:
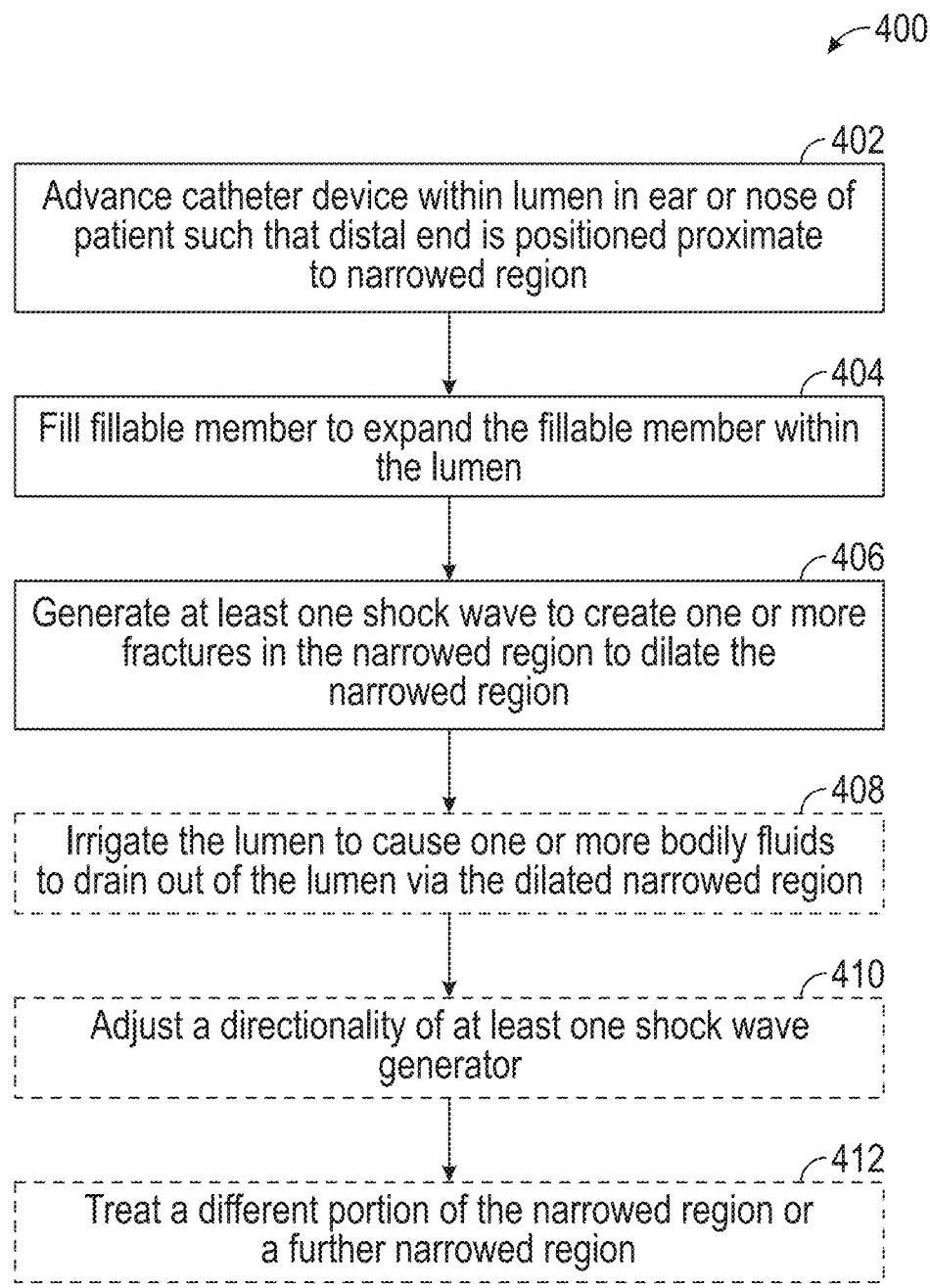
FIG. 4 illustrates a method for treating a narrowed region of a lumen in the ear or nose of a patient, according to one or more aspects of the present disclosure.

FIG. 4 illustrates a method 400 for treating a narrowed region of a lumen in the ear or nose of a patient, according to one or more aspects of the present disclosure. The method 400 can be implemented using a system having a shock wave catheter device, such as the system 10 of FIG. 1 and the catheter device 300 of FIG. 3A. The method 400 may be used to treat a narrowed region in a lumen that is part of a frontal sinus, the maxillary sinus, a sphenoid sinus, an ethmoid sinus, a sinus ostium, a turbinate (such as an inferior turbinate, a middle turbinate, or a superior turbinate), the nasal cavity, the ostiomeatal complex, or any combination thereof. The method 400 may be used to treat a narrowed region in a lumen that is part of the Eustachian tube, the external ear canal, or the middle ear.

In one or more examples, the method 400 can begin at block 402, wherein a catheter device is advanced within a lumen in the ear or nose of a patient such that a distal end of the catheter device is positioned proximate to a narrowed region in the lumen. For example, returning to FIG. 2A and FIG. 2B, the treatment region 30 is part of a lumen of the frontal sinus of a patient. FIG. 2B depicts the catheter device 35 positioned proximate to the treatment region 30 of the lumen (after the fillable member has been "inflated" or filled with conductive fluid).

In one or more examples, advancing the catheter device within the lumen such that the distal end is proximate to the narrowed region may utilize data from one or more sensors. For example, the narrowed region may be located using data from an imaging sensor of the catheter device (such as the image sensor 310 of FIG. 3A) that is processed by an external processing device to display one or more images and/or a video while the catheter device is advanced within the lumen. These images and/or video can be utilized by the surgeon while advancing the catheter device within the lumen to position the distal end proximate to the narrowed region. The distal end of the catheter device may include one or more location sensors (such as the location sensor 330 of FIG. 3B) that provide data to one or more external sensors that are external to the patient (e.g., surrounding the patient's head), which can be processed by an external processor to track the catheter device's movement within the lumen.

In one or more examples, the catheter device may be advanced within the lumen over a guidewire. The catheter device can include a lumen for receiving a guidewire, and the guidewire can be advanced within the lumen to locate the narrowed region before advancing the catheter device into the lumen to position the distal end of the catheter device proximate to the narrowed region. The guidewire may include an imaging sensor near its distal end that can be used to locate the narrowed region as above, with data from the imaging sensor processed by an external processing device to display one or more images and/or a video while the catheter device is advanced within the lumen.

In one or more examples, a separate endoscope can be advanced within the lumen. The endoscope can include an imaging sensor configured to provide imaging data that can be displayed by an external display for the surgeon to use during the shock wave procedure. Such imaging data can be used, for example, to position the distal end of the catheter device proximate to a narrowed region to be treated. For instance, the endoscope can be advanced within the lumen such that a distal end of the endoscope is proximally offset from the distal end of the catheter device (as shown in FIG. 1). Such configuration may allow the endoscope to capture imaging data of the distal end of the catheter device within the lumen, which can be used to position the distal end of the catheter device proximate to the narrowed region. Accordingly, after positioning the endoscope such that it is proximally offset from the catheter device, the endoscope can obtain one or more images of the distal end of the catheter device, which can be displayed for the surgeon.

At block 404, a fillable member of the catheter device is filled to expand the fillable member within the lumen. The fillable member can be filled with a conductive fluid, such as water or saline, which is able to conduct current flow, such as between electrodes of an electrode generator. As noted above, the fillable member may be compliant or semi-compliant such that filling the member causes the member to expand. Alternatively, the fillable member may be non-compliant such that filling the member does not cause the member to expand, or to expand nominally.

In one or more examples, filling the fillable member can comprise pressurizing the fillable member. Pressurizing the fillable member can involve introducing fluid (such as saline, water, or saline mixed with an image contrast agent) via a fluid port, such as the fluid port 26 of FIG. 1 and/or one or both of the fluid lumens 317 and 318 of FIG. 3C, allowing the fillable member to expand, and then pressurizing the fillable member to a desired pressure. In one or more examples, filling the fillable member can comprise pressurizing the fillable member to a pressure of less than ten atmospheres (10 atm). In one or more examples, filling the fillable member can comprise pressurizing the fillable member to a pressure of less than five atmospheres (5 atm). The pressure may be, for example, between approximately one atmosphere and approximately five atmospheres (1-5 atm).

At block 406, at least one shock wave is generated to create one or more fractures in the narrowed region to dilate the narrowed region. Generating shock waves can include applying one or more voltage pulses, such as via high voltage pulse generator 28 of FIG. 1, to shock wave emitters of the catheter device. Each pulse of voltage can ionize the conductive fluid inside the fillable member to create small gas bubbles around the shock wave emitter(s) that insulate the electrodes of the shock wave emitter(s). Subsequently, a plasma arc forms across a gap between electrodes of an electrode pair, creating a low impedance path where current flows freely. The heat from the plasma arc heats the conductive fluid to create a rapidly expanding vapor bubble. The expansion and collapse of the vapor bubble creates a shock wave that propagates outwardly from the shock wave emitter.

As shock waves propagate outwardly from the shock wave emitter, those shock waves impinge upon the walls of the lumen. For instance, returning again to FIG. 2B, shock waves generated from the distal end of the catheter device 35 impinge on the walls of the fontal sinus, which can create one or more fractures in the bony structure of the frontal sinus. By creating fractures in the bony structure, the lumen is free to dilate based on the diameter of the fillable member (e.g., can expand to the diameter of the "inflated" member). Accordingly, the shock waves can be used to dilate the lumen, which promotes proper drainage of fluid or mucus that was previously trapped within the body lumen due to the narrowed region. In one or more examples, these shock waves may be used to expand an area, such as to expand the treatment region 30 of FIG. 2A. Alternatively, these shock waves may be used to break off portions of the patient's anatomy, such as to impact the base of the uncinate process (shown in FIG. 2C) until the uncinate process detaches from the maxillary sinus. In further alternative implementations, the uncinate process may be weakened by shock waves such that it compresses or folds in a direction that facilitates the proper drainage of fluid or mucus, while remaining attached to the internal sinus anatomy. In one or more examples, the shock waves may break, crack, and/or otherwise treat the nasal septum. In one or more examples, in addition to or instead of the shock waves being used to expand and/or break off portions of the patient's anatomy, the diameter of the lumen may be dilated, or increased, by pressurizing the fillable member to a pressure of up to 10 atm (e.g., 4, 6, 8, or 10 atm).

In one or more examples, the pressure of the shock waves impinging on the bony structure can have an average pressure between twenty and seventy atmospheres (20-70 atm). For instance, the pressure imparted by a shock wave may be about fifty atmospheres (50 atm). Pressures in such range may dissipate as they travel further within tissues of the patient's anatomy. Nonetheless, the pressure may beneficially reach deeper into the tissues of the patient rather than remaining on the surface, and not be localized only in the area adjacent to fillable member of the catheter device. By creating shock waves that travel deeper into the patient's tissues, the shock wave treatment may result with a longer patency of the lumen. The magnitude and/or other characteristics of the shock waves can be controlled by adjusting the magnitude and/or duration of the applied voltage pulses. Embodiments of the present disclosure can be implemented using voltages from about 2000 V to about 10,000 V, and more, and increments and gradations of voltage within these ranges (e.g., 2.60 kV, 3.70 kV, 4.80 kV, 5.90 kV, 7 kV, 8.2 kV, 9.5 kV, etc.). Similarly, electrode assemblies and emitters as considered herein can be implemented using various frequencies, including frequencies between about 1 Hz and about 4 Hz, frequencies between about 4 Hz and about 10 Hz, frequencies between about 10 Hz to about 50 Hz, and increments and gradations of frequency within these ranges. The magnitude and/or duration of the applied voltage pulses can be selected based on the anatomy being treated. For example, higher voltage and/or longer voltage pulse durations can be selected for denser anatomical structures.

The characteristics of the shock waves can also be controlled by adjusting structural aspects of the electrode assembly—e.g., the distance between electrodes of an electrode pair, the surface area of the electrodes, the shape of the electrodes, etc. In some examples, the magnitude and/or other characteristics of the shock waves can be controlled for localized treatment by limiting the depth of penetration to protect sensitive anatomy beyond the treatment region 30. This may be done in any number of ways, such as by controlling the amplitude and/or frequency of voltage pulses to produce lower pressure shock waves, configuring the number and/or spacing of shock wave emitters to limit the area upon which shock waves impinge and/or limit constructive interference of shock waves, configuring the spacing of the shock wave emitters from the fillable member so that shock waves travel further within the conductive fluid within the fillable member before impinging on the treatment region 30.

In one or more examples, imaging data from an imaging sensor may be used to monitor treatment while shock waves are being generated. For example, imaging data from an imaging sensor that views the same working area where shock waves are propagating can be used to ensure the shock waves are impinging on the intended region of the lumen. In one or more examples, such imaging data can be obtained by an endoscope that is proximally offset from the distal end of the catheter device, such that the endoscope can view the impact of the shock waves from a proximal viewpoint.

In one or more examples, the method 400 can include block 408 wherein the lumen is irrigated to cause one or more bodily fluids to drain out of the lumen via the dilated narrowed region. To irrigate the lumen, the catheter device may include a separate irrigation lumen (such as the irrigation lumen 325 of FIG. 3A and FIG. 3B) that can be used to flush the patient's lumen with fluid (such as water or saline) to cause bodily fluids to drain out of the lumen via the dilated narrowed region. For instance, irrigating a lumen in the maxillary sinus or frontal sinus can encourage excess mucus to drain from the region, which may relieve symptoms of rhinosinusitis.

In one or more examples, the method 400 can include block 410 wherein a directionality of at least one shock wave emitter is adjusted. As discussed above, the catheter device can include one or more shock wave emitters that are configured to generate shock waves that propagate outwardly along a particular direction. In one or more examples, adjusting a directionality at block 410 can include rotating the catheter device about a center axis of the catheter device (such as the center axis A of FIG. 3A). To rotate the catheter device about a center axis, a surgeon may utilize an external control device, such as the control knob 23 of FIG. 1. While adjusting the directionality of at least one shock wave emitter at block 410, a surgeon may utilize image data. For example, if the catheter device includes an image sensor that obtains image data of a working area where shock waves are propagating outwardly, the surgeon may utilize such image data to ensure the working area depicted is the desired area of the lumen for shock waves to impinge upon. In one or more examples, the surgeon may utilize a separate endoscope with an image sensor and utilize data from the image sensor of the endoscope to adjust the directionality of the shock wave emitter(s) of the catheter device. In one or more examples, block 410 may be performed before block 406, that is, the directionality of at least one shock wave emitter can be adjusted before generating shock waves, so that the shock wave(s) are directed towards a particular region of the patient's lumen.

In one or more examples, the method 400 can include block 412 wherein a different portion of the narrowed region or a further narrowed region is treated. Treating a different portion of the narrowed region can include rotating the catheter device as described above such that shock waves impinge on a new portion of the lumen (e.g., the opposite side of the lumen). Treating a further narrowed region can involve repeating one or more steps of blocks 402, 404, 406, 408, and/or 410, and may include advancing the catheter device to the further narrowed region, filling the fillable lumen, and generating at least one shock wave to create one or more fractures in the further narrowed region. To advance the catheter device to a further narrowed region, the surgeon may first evacuate the fluid from the fillable member to reduce the outer diameter of the distal end of the catheter device, and the surgeon may then re-fill the fillable member once the distal end of the catheter device is positioned proximate to the further narrowed region.

Figure 5:
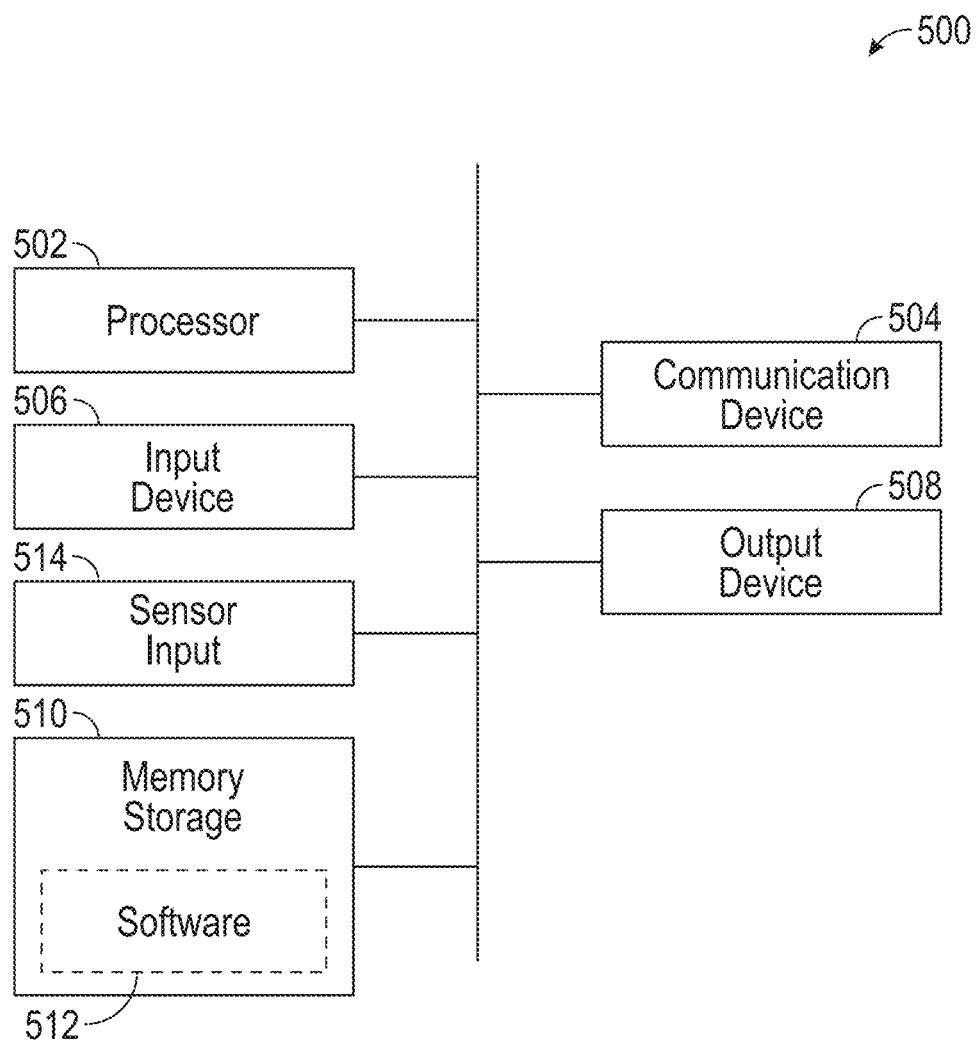
FIG. 5 illustrates an exemplary computing device, according to one or more aspects of the present disclosure.

FIG. 5 shows an exemplary computing device 500, according to one or more examples of the disclosure. Device 500 can be a component of a system for treating a narrowed region of a lumen in the ear or nose of a patient, such as system 10 of FIG. 1. In one or more examples, device 500 is configured to process sensor input 514, such as image data from an image sensor such as the image sensor 310 of FIG. 3A and/or an imager such as the endoscopic imager 29 of system 10 of FIG. 1 to display image data to a surgeon for positioning and/or orienting a catheter device to treat a narrowed region of a lumen. In one or more examples, the sensor input 514 includes location data from one or more location sensors such as the location sensor 330 of FIG. 3B for positioning and/or orienting a catheter device within a lumen of a patient's ear or nose. In another examples, the sensor input 514 includes navigation data from one or more navigation sensors (e.g., radiofrequency or electromagnetic sensors) that indicate the position of the guidewire and/or catheter within the body lumen on a visual display.

Device 500 can be a host computer connected to a network. Device 500 can be a client computer or a server. As shown in FIG. 5 device 500 can be any suitable type of microprocessor-based device, such as a personal computer, workstation, server, or handheld computing device (portable electronic device) such as a phone or tablet. The device can include, for example, one or more of processors 502, input device 506, output device 508, storage 510, and communication device 504. Input device 506 and output device 508 can generally correspond to those described above and can either be connectable or integrated with the computer.

Input device 506 can be any suitable device that provides input from an operator of the device, such as a touch screen, keyboard or keypad, mouse, or voice-recognition device. Input device 506 may additionally or alternatively be configured to receive data stored on a separate or connected computerized device, where in the context of sinus anatomy such data can be, for example, calibration or orientation data for a specific patient. Output device 508 can be any suitable device that provides output, such as a touch screen, haptics device, or speaker.

Storage 510 can be any suitable device that provides storage, such as an electrical, magnetic, or optical memory, including a RAM, cache, hard drive, or removable storage disk. Communication device 504 can include any suitable device capable of transmitting and receiving signals over a network, such as a network interface chip or device. The components of the computer can be connected in any suitable manner, such as via a physical bus or wirelessly.

Software 512, which can be stored in storage 510 and executed by processor 502, can include, for example, the programming that embodies the functionality of the present disclosure (e.g., as embodied in the devices as described above). Software 512 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 510, that can contain or store programming for use by or in connection with an instruction execution system, apparatus, or device.

Software 512 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate, or transport programming for use by or in connection with an instruction execution system, apparatus, or device. The transport readable medium can include, but is not limited to, an electronic, magnetic, optical, electromagnetic, or infrared wired or wireless propagation medium.

Device 500 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Device 500 can implement any operating system suitable for operating on the network. Software 512 can be written in any suitable programming language, such as C, C++, Java, or Python. In various embodiments, application software embodying the functionality of the present disclosure can be deployed in different configurations, such as in a client/server arrangement or through a Web browser as a Web-based application or Web service, for example.

Although the catheter devices described herein may have been discussed primarily in the context of treating coronary indications, such as lesions in vasculature, the catheter devices described herein can be used for a variety of indications. For instance, similar designs could be used for treating soft tissues, such as cancer and tumors (i.e., non-thermal ablation methods), blood clots, fibroids, cysts, organs, scar and fibrotic tissue removal, or other tissue destruction and removal treatments. Catheter devices could be used for neurostimulation treatments, targeted drug delivery, treatments of tumors in body lumens (e.g., tumors in blood vessels, the esophagus, intestines, stomach, or vagina), wound treatment, non-surgical removal and destruction of tissue, or used in place of thermal treatments or cauterization for venous insufficiency and fallopian ligation (i.e., for permanent female contraception). Further, the catheter devices described herein could also be used for tissue engineering methods, for instance, for mechanical tissue decellularization to create a bioactive scaffold in which new cells (e.g., exogenous and endogenous cells) can replace the old cells; introducing porosity to a site to improve cellular retention, cellular infiltration/migration, and diffusion of nutrients and signaling molecules to promote angiogenesis, cellular proliferation, and tissue regeneration similar to cell replacement therapy. Such tissue engineering methods may be useful for treating ischemic heart disease, fibrotic liver, fibrotic bowel, and traumatic spinal cord injury (SCI). For instance, for the treatment of spinal cord injury, the devices and assemblies described herein could facilitate the removal of scarred spinal cord tissue, which acts like a barrier for neuronal reconnection, before the injection of an anti-inflammatory hydrogel loaded with lentivirus to genetically engineer the spinal cord neurons to regenerate.

It should be noted that the elements and features of the example catheters illustrated throughout this specification and drawings may be rearranged, recombined, and modified without departing from the present invention. The number, placement, and spacing of the electrode pairs of the shock wave emitters can be modified without departing from the subject invention. Further, the number, placement, and spacing of balloons of catheters can be modified without departing from the subject invention.

It will be understood that the foregoing is only illustrative of the principles of the invention, and that various modifications, alterations and combinations can be made by those skilled in the art without departing from the scope and spirit of the invention. Any of the variations of the various catheter devices disclosed herein can include features described by any other catheter devices or combination of catheter devices herein. Furthermore, any of the methods can be used with any of the catheter devices disclosed. Accordingly, it is not intended that the invention be limited, except as by the appended claims.

The invention claimed is:

1. A method for treating a narrowed region of a lumen in the ear or nose of a patient, the method comprising:
    advancing a catheter within the lumen such that a distal end of the catheter is positioned proximate to the narrowed region, the distal end of the catheter comprising at least one shock wave emitter that is surrounded by a fillable member;
    filling the fillable member to expand the fillable member within the lumen; and
    generating at least one shock wave from the at least one shock wave emitter, the at least one shock wave creating one or more fractures in a bony structure of the narrowed region of the lumen that dilate the narrowed region.

2. The method of claim 1, comprising irrigating the lumen to cause one or more bodily fluids to drain out of the lumen via the dilated narrowed region.

3. The method of claim 1, comprising adjusting a directionality of the at least one shock wave emitter prior to generating the one or more shock waves so that the at least one shock wave is directed toward the bony structure.

4. The method of claim 3, wherein adjusting the directionality of the at least one shock wave emitter comprises rotating the catheter within the lumen about a center axis of the catheter.

5. The method of claim 3, wherein adjusting the directionality of the at least one shock wave emitter comprises adjusting an external knob of the catheter to cause the catheter to rotate within the lumen about a center axis of the catheter.

6. The method of claim 3, wherein adjusting the directionality of the at least one shock wave emitter comprises adjusting the catheter such that an external indicator is oriented along a desired direction.

7. The method of claim 1, wherein the fillable member comprises a semi-compliant balloon or compliant balloon.

8. The method of claim 1, wherein filling the fillable member comprises pressurizing the fillable member to a pressure of less than 10 atm.

9. The method of claim 1, wherein filling the fillable member comprises pressurizing the fillable member to a pressure of up to 6 atm.

10. The method of claim 1, comprising, after generating the at least one shock wave, increasing the diameter of the lumen in the ear or the nose of the patient by pressurizing the fillable member to a pressure of up to 10 atm.

11. The method of claim 1, comprising:
    at least partially collapsing the fillable member;
    advancing the catheter further within the lumen such that the distal end of the catheter is positioned proximate to a different portion of the narrowed region or a further narrowed region;
    filling the fillable member to expand the fillable member within the lumen; and
    generating at least one shock wave from the at least one shock wave emitter, the at least one shock wave creating one or more fractures in the further narrowed region of the lumen to dilate the further narrowed region.

12. The method of claim 1, wherein advancing the catheter within the lumen comprises advancing the catheter over a guidewire.

13. The method of claim 1, wherein the lumen is part of a frontal sinus, a maxillary sinus, a sphenoid sinus, an ethmoid sinus, a sinus ostium, an inferior turbinate, a middle turbinate, a superior turbinate, a nasal cavity, the ostiomeatal complex, or a combination thereof.

14. The method of claim 1, comprising locating the narrowed region using an imaging sensor of the catheter prior to generating the at least one shock wave.

15. The method of claim 1, comprising:
    advancing an endoscope within the lumen such that a distal end of the endoscope is proximally offset from the distal end of the catheter; and
    obtaining one or more images of the distal end of the catheter to locate the narrowed region.

16. The method of claim 1, wherein the at least one shock wave delivers a therapeutically effective amount of an active agent of a drug to the lumen.

17. The method of claim 16, wherein the active agent comprises a corticosteroid.

18. The method of claim 16, wherein the active agent comprises an antibiotic.

19. The method of claim 16, wherein a drug layer on the fillable member comprises the active agent and one or more adjunctive agents.

20. A device for treating a narrowed region of a lumen in the ear or nose of a patient, the device comprising:
    an elongated tube;
    at least one shock wave emitter, the at least one shock wave emitter configured to generate at least one shock wave along a working direction;
    at least one imaging sensor oriented to capture images along the working direction; and
    a fillable member sealed to a distal end of the elongated tube and surrounding the at least one shock wave emitter and the at least one imaging sensor, the fillable member fillable with a conductive fluid.

21. The device of claim 20, wherein the fillable member comprises a drug coating, and the least one shock wave delivers a therapeutically effective amount of an active agent of a drug to the lumen.

* * * * *